United States Patent
Lum et al.

(10) Patent No.: US 7,109,330 B2
(45) Date of Patent: *Sep. 19, 2006

(54) PURINE INHIBITORS OF CYCLIN DEPENDENT KINASE 2 AND IκB-α

(75) Inventors: Robert Lum, Palo Alto, CA (US); Cheri Lynn Blum, Alameda, CA (US); Richard Mackman, San Bruno, CA (US); Michael Wick, Portola Valley, CA (US); Steven Schow, Redwood Ciy, CA (US); Jeff Zablocki, Mountain View, CA (US); Prabha Ibrahim, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/794,828

(22) Filed: Mar. 3, 2004

(65) Prior Publication Data

US 2005/0080261 A1   Apr. 14, 2005

Related U.S. Application Data

(63) Continuation of application No. 09/929,772, filed on Aug. 14, 2001, now Pat. No. 6,790,958, which is a continuation-in-part of application No. 09/230,829, filed on Aug. 30, 1999, which is a continuation of application No. 09/241,224, filed as application No. PCT/US97/13386 on Aug. 1, 1997, now abandoned, which is a continuation of application No. 08/692,012, filed on Aug. 2, 1996, now Pat. No. 5,866,702.

(51) Int. Cl.
C07D 473/16 (2006.01)
C07D 473/40 (2006.01)
A61K 31/53 (2006.01)
A61P 35/00 (2006.01)
A61P 3/10 (2006.01)

(52) U.S. Cl. .................................. 544/277
(58) Field of Classification Search .......... 514/263.2, 514/263.22, 263.4; 544/277
See application file for complete search history.

(56) References Cited

U.S. PATENT DOCUMENTS 5,866,702 A * 2/1999 Mackman et al. ......... 544/277
6,303,618 B1 * 10/2001 Griffin et al. ............. 544/277
6,316,456 B1 * 11/2001 Meijer et al. .............. 544/265
6,498,163 B1 * 12/2002 Boschelli et al. ........ 514/264.1
6,767,906 B1 * 7/2004 Imbach et al. ........... 514/234.2
6,794,390 B1 * 9/2004 Lum et al. ............... 514/263.2
6,803,371 B1 * 10/2004 Gray et al. .............. 514/263.4
2005/0009846 A1 * 1/2005 Fischer et al. ........... 514/263.4

FOREIGN PATENT DOCUMENTS

WO    WO 97/16452    * 5/1997

OTHER PUBLICATIONS

Vesely, Eur. J. Biochem. 224, 771 (1994).*
Glab, FEBS Letters 353, 207 (1994).*
Abraham, Biol Cell 83, 105 (1995).*
Schultz-Gahmen, Proteins: Structure, function and Genetics 22, 378 (1995).*
Schow, Biorganic & Medicinal Chemistry Letters 7(21) 2967, 1997.*
Kenneth A. Jacobson, J Med. Chem 38(10) pp. 1720-1735 (1995).*
Thais M. Sielecki, J. Med. Chem.; 2000; 43(1) pp. 1-18.*

* cited by examiner

Primary Examiner—Mark L. Berch
(74) Attorney, Agent, or Firm—CV Therapeutics, Inc.

(57) ABSTRACT

Compounds of the following formula are provided:

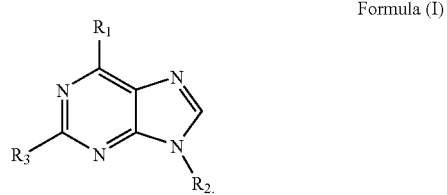

Formula (I)

In the Formula (I), $R_1$ is —X—$R_1'$; in which $R_1'$ is optionally substituted lower alkyl, optionally substituted aryl, optionally substituted heteroaryl, or optionally substituted heterocyclyl, and X is —NH—. $R_2$ is lower alkyl optionally substituted with one, two or three groups chosen from hydroxy, lower alkoxy, and halogen. And $R_3$ is —$NR_4R_5$; in which $R_4$ is hydrogen and $R_5$ is lower alkyl substituted with amino; or (ii) $R_4$ and $R_5$ are both lower alkyl optionally substituted with one, two or three groups chosen from hydroxy and amino. It is to be understood that $R_1'$ is not cyclohexylmethyl, phenyl, substituted phenyl, benzyl, phenylethyl, or m-hydroxybenzyl. The compounds inhibit CDK-2 activity and are useful for treating disorders characterized by undesirable cell proliferation.

3 Claims, 1 Drawing Sheet

SEQUENCE LISTING

<160> NUMBER OF SEQ ID NOS: 1

<210> SEQ ID NO 1
<211> LENGTH: 22
<212> TYPE: DNA
<213> ORGANISM: unknown
<220> FEATURE:
<223> OTHER INFORMATION: double stranded NF-kappa B consenses oligonucleotide

<400> SEQUENCE: 1
agttgagggg actttcccag gc                                          22

PURINE INHIBITORS OF CYCLIN DEPENDENT KINASE 2 AND IκB-α

This application is a continuation of U. S. patent application Ser. No. 09/929,772, filed on Aug. 14, 2001, now U.S. Pat. No. 6,790,958, which is a continuation of U.S. patent application Ser. No 091241,224, filed on Feb. 1, 1999 and now abandoned, which is a continuation-in-part of U. S. patent application Ser. No. 09/230,829, which is a §371 filing of PCT Application PCT/US97/13386, filed on Aug. 1, 1997, now abandoned, which is a continuation-in-part of U. S. patent application Ser. No. 08/692,012, filed on Aug. 2, 1996, now U.S. Pat. No. 5,866,702.

BACKGROUND OF THE INVENTION

1. Field of the Invention

This invention concerns 2,6,9-trisubstituted purines that have been discovered to be selective inhibitors of cell cycle kinases and, as such, the compounds are inhibitors of cell proliferation. The 2,6,9-trisubstituted purines are useful in for example in—treating autoimmune diseases, e.g. rheumatoid arthritis, lupus, type I diabetes, multiple sclerosis, etc., in treating cancer, cardiovascular disease, such as restenosis, host vs graft disease, gout, polycystic kidney disease and other proliferative diseases whose pathogenesis involves abnormal cell proliferation.

This invention also concerns 2,6,9-trisubstituted purines that have been discovered to be potent and specific inhibitors of IκB-α kinase that prevents signal induced NF-κB activation and cytokine synthesis in vitro and in vivo. Such inhibitors are expected to inhibit the synthesis of cytokines and adhesion proteins whose synthesis is transcriptionally regulated by NF-κB. Proinflammatory cytokines such as 1L-1, 1L-6, TNF and adhesion proteins (e.g. ICAM, VCAM and selections) belong to this class of molecules and have been implicated in the pathogenesis of inflammatory diseases. Thus, a potent inhibitor of IκB-α kinase is useful in the clinical management of diseases where NF-κB activation is required for disease induction.

2. Description of the Art

In the past few years, advances in molecular and cellular biology have contributed to our understanding of the mechanisms of cell proliferation and of specific events that occur during progression of cells through mitosis, e.g., "Progress in Cell Cycle Research" Vol 1, Eds. L. Meijer, S. Guidet and H. Y. L. Tung; Plenum Press, New York, 1995. These studies have shown that progression through the cell cycle is controlled by a family of serine/threonine kinases called cyclin dependent kinases. These enzymes contain (a) a catalytic protein called cyclin dependent kinase (CDK) that uses ATP as a substrate and (b) a regulatory protein called cyclin. Different cyclin-CDK combinations control events such as growth, DNA replication, and cell division. One key member of the CDK family of enzymes is CDK2. CDK2 activity has been shown to be essential for mammalian cell cycle progression at the G1/S boundary. Microinjection of antibodies directed against CDK2 blocks the progression of human diploid fibroblasts into the S phase of the cell cycle. Expression of a CDK2 dominant negative mutant in human osteosarcoma cells has a similar effect. Together, these studies indicate that inhibition of cellular CDK2 activity will prevent progression of cells through the mitotic cycle and induce growth arrest prior to the S phase. Consistent with this view, in vitro studies with olomoucine (2-(hydroxyethylamino)-6-benzylamino-9-methylpurine), have shown that it is a specific inhibitor of CDK2 with an $IC_{50}$ of approximately 2.1 μg/ml J. Vesely, et al.; Eur. J. Biochem 224, 771–786 (1994), L. Meijer "Chemical Inhibitors of Cyclin-Dependent Kinases" pp 351–356 in "Progress in Cell Cycle Research Vol 1, Eds. L. Meijer, S. Guidet and H. Y. L. Tung; Plenum Press, New York, 1995. In vivo studies using mammalian cells in culture have shown that olomoucine inhibits cell proliferation at an approximate concentration of 50 μg/ml.

In this invention, we have developed several compounds whose biological activity is considerably more potent than olomoucine. In vivo studies using mammalian cells indicate that some of the disclosed compounds inhibit cell proliferation at concentrations that are significantly lower than olomoucine.

Recently an IκB-α kinase activity has been described in the cytoplasm of stimulated human umbilical vein endothelial cells (Bennett et al (1996) J. Biol. Chem 271, 19680–19688). Some of the compounds of this invention have been identified as potent and specific inhibitors of IκB-α kinase that prevents signal induced NF-κB activation and cytokine synthesis in vitro and in vivo. The activation of the heterodimeric transcription factor NF-κB is a complex process. In unstimulated cells, the NF-κB (p50/p65) heterodimer is located in the cytosol where it is complexed with an inhibitory subunit IκB-α, IκB-α, binds to NF-κB thus masking its nuclear localization signal and preventing translocation to the nucleus. Upon stimulation of cells with a variety of signals (e.g. lipopolysaccharide) IκB-α is rapidly phosphorylated, uniquitinated and degraded by the proteasome. Degradation of IκB-α, allows the translocation of NF-κB to the nucleus where it activates transcription of a number of inflammatory response genes.

These observations suggest that IκB-α kinase is an attractive target for the identification of inhibitors that may be useful in the treatment of inflammatory diseases where NF-κB activation is required for disease induction.

SUMMARY OF THE INVENTION

It is an object of this invention to provide 2,6,9-trisubstituted purine compounds, which inhibit the cyclin dependent kinase 2.

It is another object of this invention to provide 2,6,9-trisubstituted purine compounds that are useful for inhibiting cell proliferation.

This invention also constitutes a pharmaceutical composition, which comprises a 2,6,9-trisubstituted purine compound and a pharmaceutically acceptable carrier.

This invention further constitutes a method for inhibiting cell proliferation, which comprises administering to a mammal in need thereof an effective amount of a 2,6,9-trisubstituted purine compound.

In one embodiment, this invention is A 2,6,9-trisubstituted purine composition of matter having the following formula:

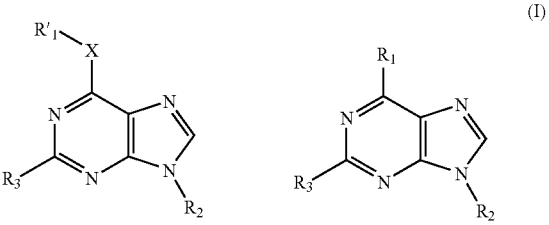

wherein $R_1$ is halogen or $R'_1$—X wherein X=NH, O, S, $S(O_2)$. In the composition, $R'_1$ is alkyl, heterocyclyl, aryl, heteroaryl, aralkyl, heteroarylalkyl, alkenyl, and alkynyl, each having one to 20 carbon atoms, which alkyl, heterocyclyl, aryl, heteroaryl, aralkyl, heteroarylalkyl, alkenyl, and alkynyl, are optionally substituted with from 1 to 3 substituents independently selected from the group consisting of halo, aryl, $CF_3$, heteroaryl, heterocyclyl, $R^{22}$, $SR^{20}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $SO_2NR^{20}CO_2R^{21}$, $NR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $NR^{20}SO_2R^{21}$, $OR^{20}$, $OCONR^{20}R^{23}$, $OCONR^{20}SO_2R^{21}$, $OCONR^{20}R^{23}$, CN, $CO_2R^{20}$, $CONR^{20}R^{23}$, $CONR^{20}SO_2R^{21}$ and $COR^{20}$. Also in the composition, $R_2$ is a hydrogen or hydrocarbon selected from the group alkyl, heterocyclyl, aryl, heteroaryl, aralkyl, heteroarylalkyl, alkenyl, and alkynyl, each having one to 20 carbon atoms, which alkyl, heterocyclyl, aryl, heteroaryl, aralkyl, heteroarylalkyl, alkenyl, and alkynyl, are optionally substituted with from 1 to 3 substituents independently selected from the group consisting of halo, aryl, heteroaryl, heterocyclyl, $R^{22}$, $SR^{20}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $SO_2NR^{20}CO_2R^{21}$, $NR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $NR^{20}SO_2R^{21}$, $OR^{20}$, $OCONR^{20}R^{23}$, $OCONR^{20}SO_2R^{21}$, $OCONR^{20}R^{23}$, CN, $CO_2R^{20}$, $CONR^{20}R^{23}$, $CONR^{20}SO_2R^{21}$ and $COR^{20}$.

Further, in the compositions, $R_3$ is a halogen, hydroxyl, thio, alkoxy, alkylthio, alkyl, —$NR_4R_5$ or a component having the formula:

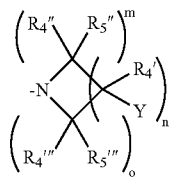

where m=1–3, n=1–3, o=1,3, y=carbonyl, —$NR_4R_5$, hydroxyl, thiol, $R_4$ and $R_5$ are each independently hydrogen, $OR_{20}$, $NR_{20}R_{23}$, or a hydrocarbon selected from the group including alkyl, acyl, heterocyclyl, aryl, heteroaryl, aralkyl, heteroarylalkyl, alkenyl, and alkynyl, each having one to 20 carbon atoms, which alkyl, acyl, heterocyclyl, aryl, heteroaryl, aralkyl, heteroarylalkyl, alkenyl, and alkynyl, are optionally substituted with from 1 to 3 substituents independently selected from the group consisting of halo, aryl, heteroaryl, heterocyclyl, $R^{22}$, $SR^{20}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $SO_2NR^{20}CO_2R^{21}$, $NR^{20}R^{23}$, $NR^{20}COR^{21}$, $NR^{20}CO_2R^{23}$, $NR^{20}CONR^{20}R^{23}$, $N(R^{20})C(NR^{20})NHR^{23}$, $NR^{20}SO_2R^{21}$, $OR^{20}$, $OCONR^{20}R^{23}$, $OCONR^{20}SO_2R^{21}$, $OCONR^{20}R^{23}$, CN, $CO_2R^{20}$, $CONR^{20}R^{23}$, $CONR^{20}SO_2R^{21}$ and $COR^{20}$;

$R^{20}$ is a member selected from the group consisting of H, $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, monoor dialkylamino, alkyl or aryl or heteroaryl amide, CN, O—$C_{1-6}$ alkyl, $CF_3$, aryl, and heteroaryl;

$R^{21}$ is a member selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}SO_2NR^{20}CON(R^{20})_2$, $N(R^{20})_2$, $NR^{20}COR^{22}$, $NR^{20}CO_2R^{22}$, $NR^{20}CON(R^{20})_2$ $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OR^{20}$, $OCONR^{20}SO_2R^{22}$, $OC(O)R^{20}$, $C(O)OCH_2OC(O)R^{20}$, and $OCON(R^{20})_2$, and each optional heteroaryl, aryl, and heterocyclyl substituent is optionally substituted with halo, alkyl, $CF_3$, amino, monoor di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^{22}$ is a member selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, monoor dialkylamino, alkyl or aryl or heteroaryl amide, CN, O—$C_{1-6}$ alkyl, $CF_3$, aryl, and heteroaryl; and $R^{23}$ is $R^{21}$ or H.

There are some limitations to the scope of the compositions of this invention. When Y is carbonyl, Y and $R'_4$ together may be a single oxygen atom, $R_4''$ and $R_5''$ together may be a single oxygen atom, $R_4'''$ and $R_5'''$ may together be a single oxygen atom. When $R_3$ is 2-hydroxyethylamino and $R_2$ is methyl, $R_1'$—X is not amino, 3-methyl-2-butenylamino, benzylamino, or m-hydroxybenzylamino when $R_3$ is not 2-hydroxyethylamino. When $R_2$ is isopropyl, $R_1'$—X is not benzylamino, m-hydroxybenzylamino, or 3-methylbutylamino. When $R_3$ is 2-hydroxyethylamino and $R_2$ is 2-hydroxyethyl, $R_1'$—X is not benzylamino and when $R_3$ is selected from the group consisting of 2-methyl-2-hydroxypropylamino, and 2-dimethylaminoethylamino, and when $R_2$ is methyl, then $R_1'$—X is not benzylamino In another embodiment, this invention is a method for inhibiting cell proliferation in mammals comprising administering a therapeutically effective amount of the composition of claim 1 to the mammal. The method is useful for treating cell proliferation disorders such as rheumatoid arthritis, lupus, type I diabetes, multiple sclerosis, cancer, restenosis, host graft disease, and gout.

In yet another embodiment, this invention is a pharmaceutical composition of matter comprising the composition above in an admixture with one or more pharmaceutical excipients.

In still another embodiment, this invention is a composition useful for treating fungal infections (fungi) in humans, animals, and in plants.

DESCRIPTION OF THE CURRENT EMBODIMENT

Figure 1:
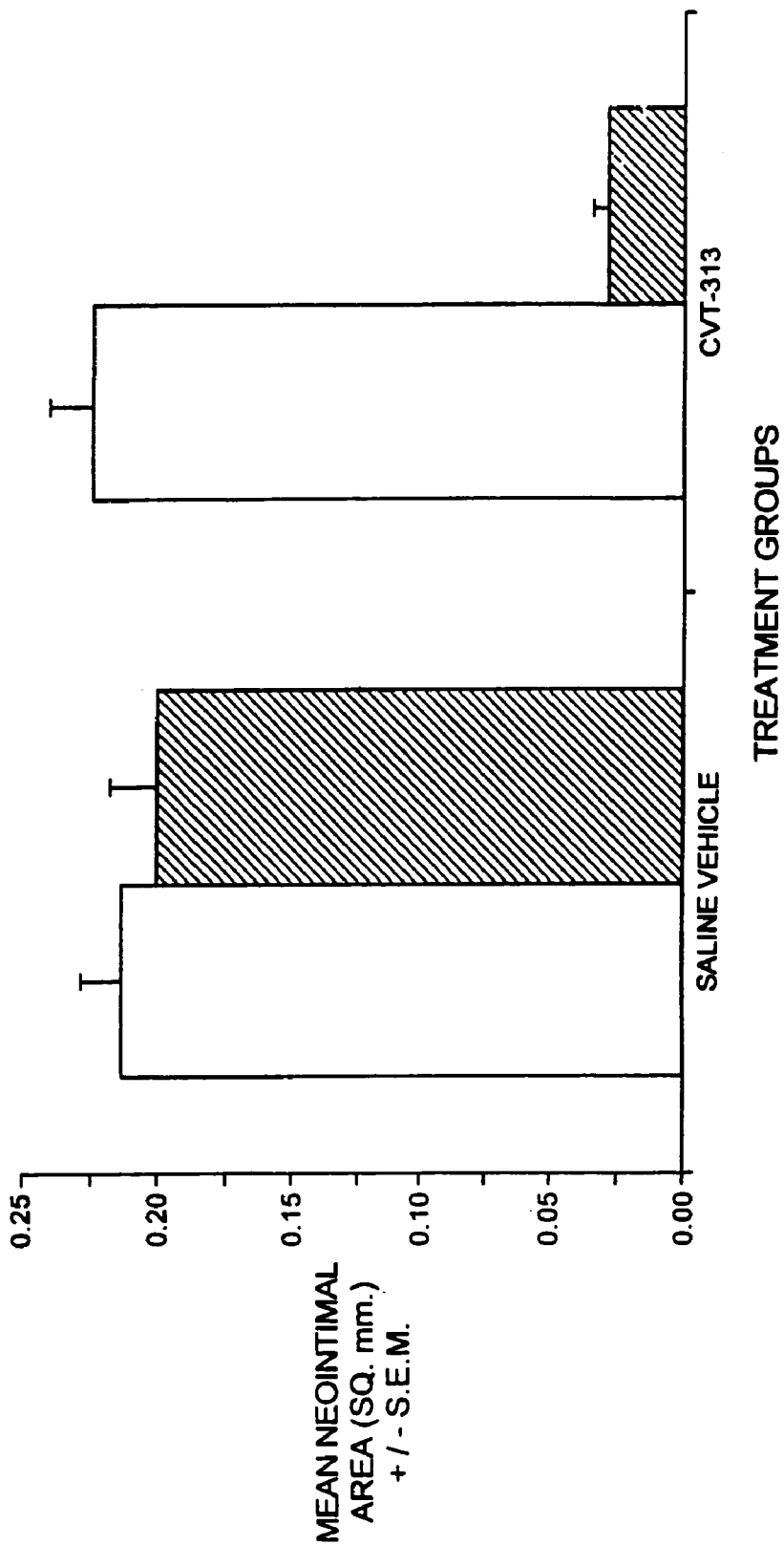
FIG. 1 is a plot of the mean neointimal area of a rat carotid artery treated with a saline vehicle and treated with compound 3 prepared according to Example 2 wherein the unshaded bar represents the untreated section of the carotid artery and the shaded bar represents the treated section of the carotid artery.

The present invention relates to a 2,6,9-trisubstituted purine compound having the following formulas:

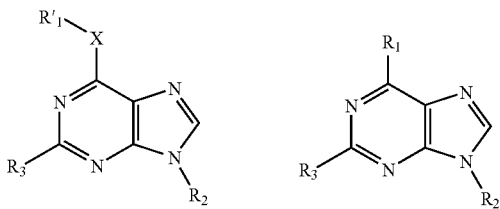

where:

$R_1$ is halogen or $R'_1$—X wherein X=NH, O, S, S(O$_2$).

$R'_1$ is alkyl, heterocyclyl, aryl, heteroaryl, aralkyl, heteroarylalkyl, alkenyl, and alkynyl, each having one to 20 carbon atoms, which alkyl, heterocyclyl, aryl, heteroaryl, aralkyl, heteroarylalkyl, alkenyl, and alkynyl, are optionally substituted with from 1 to 3 substituents independently selected from the group consisting of halo, aryl, CF$_3$, heteroaryl, heterocyclyl, $R^{22}$, $SR^{20}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $SO_2NR^{20}CO_2R^{21}$, $NR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $NR^{20}SO_2R^{21}$, $OR^{20}$, $OCONR^{20}R^{23}$, $OCONR^{20}SO_2R^{21}$, $OCONR^{20}R^{23}$, CN, $CO_2R^{20}CONR^{20}R^{23}$, $CONR^{20}SO_2R^{21}$ and $COR^{20}$;

$R_2$ is a hydrogen or hydrocarbon selected from the group alkyl, heterocyclyl, aryl, heteroaryl, aralkyl, heteroarylalkyl, alkenyl, and alkynyl, each having one to 20 carbon atoms, which alkyl, heterocyclyl, aryl, heteroaryl, aralkyl, heteroarylalkyl, alkenyl, and alkynyl, are optionally substituted with from 1 to 3 substituents independently selected from the group consisting of halo, aryl, heteroaryl, heterocyclyl, $R^{22}$, $SR^{20}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $SO_2NR^{20}CO_2R^{21}$, $NR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $NR^{20}SO_2R^{21}$, $OR^{20}$, $OCONR^{20}R^{23}$, $OCONR^{20}SO_2R^{21}$, $OCONR^{20}R^{23}$, CN, $CO_2R^{20}$, $CONR^{20}R^{23}$, $CONR^{20}SO_2R^{21}$ and $COR^{20}$;

$R_3$ is a halogen, hydroxyl, thio, alkoxy, alkylthio, alkyl, —$NR_4R_5$ or a component having the formula:

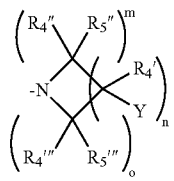

where m=1–3, n=1–3, o=1,3, y=carbonyl, —$NR_4R_5$, hydroxyl, thiol, alkoxy, alkylthiol;

$R_4$ and $R_5$ are each independently hydrogen, $OR_{20}$, $NR_{20}R_{23}$, or a hydrocarbon selected from the group including alkyl, acyl, heterocyclyl, aryl, heteroaryl, aralkyl, heteroarylalkyl, alkenyl, and alkynyl, each having one to 20 carbon atoms, which alkyl, acyl, heterocyclyl, aryl, heteroaryl, aralkyl, heteroarylalkyl, alkenyl, and alkynyl, are optionally substituted with from 1 to 3 substituents independently selected from the group consisting of halo, aryl, heteroaryl, heterocyclyl, $R^{22}$, $SR^{20}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $SO_2NR^{20}CO_2R^{21}$, $NR^{20}R^{23}$, $NR^{20}COR^{21}$, $NR^{20}CO_2R^{21}$, $NR^{20}CONR^{20}R^{23}$, $N(R^{20})C(NR^{20})NHR^{23}$, $NR^{20}SO_2R^{21}$, $OR^{20}$, $OCONR^{20}R^{23}$, $OCONR^{20}SO_2R^{21}$, $OCONR^{20}R^{23}$, CN, $CO_2R^{20}$, $CONR^{20}R^{23}$, $CONR^{20}SO_2R^{21}$ and $COR^{20}$; with the proviso that when Y is carbonyl, Y and $R'_4$ together may be a single oxygen atom, $R_4''$ and $R_5''$ together may be a single oxygen atom, $R_4'''$ and $R_5'''$ may together be a single oxygen atom, and wherein when $R_3$ is 2-hydroxyethylamino and $R_2$ is methyl, $R_1'$—X is not amino, 3-methyl-2-butenylamino, benzylamino, or m-hydroxybenzylamino, when $R_3$ is not 2-hydroxyethylamino, when $R_2$ is isopropyl, $R_1'$—X is not benzylamino, m-hydroxybenzylamino, or 3-methylbutylamino, when $R_3$ is 2-hydroxyethylamino and $R_2$ is 2-hydroxyethyl, $R_1'$—X is not benzylamino and when $R_3$ is selected from the group consisting of 2-methyl-2-hydroxypropylamino, and 2-dimethylaminoethylamino, and when $R_2$ is methyl, then $R_1'$—X is not benzylamino.

In the compositions, $R^{20}$ is a member selected from the group consisting of H, $_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, CF$_3$, aryl, and heteroaryl.

Also in the compositions, $R^{21}$ is a member selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, heterocyclyl, aryl, heteroaryl, CF$_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20}NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OR^{20}$, $OCONR^{20}SO_2R^{22}$, OC(O)$R^{20}$, C(O)OCH$_2$OC(O)$R^{20}$, and OCON($R^{20}$)$_2$, and each optional heteroaryl, aryl, and heterocyclyl substituent is optionally substituted with halo, alkyl, CF$_3$, amino, mono- or dialkylamino, alkyl or aryl or heteroaryl amide, NCOR$^{22}$, $NR^{20}SO_2R^{22}$, COR$^{20}$, CO$_2R^{20}$, CON($R^{20}$)$_2$, $NR^{20}CON(R^{20})_2$, OC(O)$R^{20}$, OC(O)N($R^{20}$)$_2$, $SR^{20}$, $S(O)R^{22}$, $SO_2R^{22}$, $SO_2N(R^{20})_2$, CN, or $OR^{20}$.

In the compositions, $R^{22}$ is a member selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are optionally substituted with 1 to 3 substituents independently selected from halo, alkyl, mono- or dialkylamino, alkyl or aryl or heteroaryl amide, CN, O—$C_{1-6}$ alkyl, CF$_3$, aryl, and heteroaryl, and $R^{23}$ is $R^{21}$ or H.

$R'_1$ is preferably an aryl, substituted aryl, each having 6 carbon atoms wherein substitution includes optional substitution with from 1 to 2 substituents independently selected from the group consisting of halo, CF$_3$, aryl, $R^{22}$, $NR^{20}R^{23}$, $NR^{20}COR^{21}$, $OR^{20}$, CN; an aralkyl, substituted aralkyl, each having 6–8 carbon atoms wherein substitution includes optional substitution with from 1 to 2 substituents independently selected from the group consisting of halo, CF$_3$, aryl, $R^{22}$, $NR^{20}R^{23}$, $NR^{20}COR^{21}$, $OR^{20}$, CN; —CH$_2$-phenyl wherein the phenyl ring is optionally substituted with from 1 to 2 substituents independently selected from the group consisting of halo, CF$_3$, $R^{22}$, $OR^{20}$, CN; substituted pyridylalkyl; unsubstituted pyridylalkyl; pyridyl; substituted pyridyl; and benzyl substituted with a halogen, alkoxy, phenyl, pyridyl or nitro group. In some compositions, $R'_1$ is preferably CH$_2$— aryl or CH$_2$— substituted aryl. Most preferably, $R_1'$ is selected from 3-methylthiophenyl, 4-methylthiophenyl, 4-phenylbenzyl, 4-methoxybenzyl, 4-biphenyl, 3-methoxybenzyl, 4-(2-thienyl)benzyl, 4-(4-methyl)phenylbenzyl, 4-(4-trifluoromethyl)phenylbenzyl, 4-(4-nitrilo)phenylbenzyl, 4-(2-pyridinyl)benzyl, piperonyl, 3-methoxbenzyl, 4-chlorobenzyl, and 4-nitrobenzyl.

$R_2$ is preferably hydrogen or a hydrocarbon selected from the group substituted lower alkyl, cycloalkyl, substituted cycloalkyl each having one to 6 carbon atoms wherein substitution includes optional substitution with from 1 to 2 substituents independently selected from the group consisting of halo, $R^{22}$, $NR^{20}R^{23}$, $OR^{20}$; substituted alkyl, cycloalkyl, substituted cycloalkyl each having one to 6 carbon atoms wherein substitution includes optional substitution with from 1 to 2 substituents independently selected from the group consisting of halo, $R^{22}$, $NR^{20}R^{23}$, and $OR^{20}$. More preferably, $R_2$ is isopropyl.

$R_3$ is preferably —$NR_4R_5$ wherein $R_4$ and $R_5$ are each selected from the group consisting of hydrogen, alkyl, heterocyclyl, acyl, aryl, heteroaryl, aralkyl, heteroaralkyl, alkyl alkenyl, alkyl alkynyl, each having one to 20 carbon atoms, which alkyl, acyl, heterocyclyl, aryl, heteroaryl, aralkyl, heteroarylalkyl,are optionally substituted with from 1 to 3 substituents independently selected from the group consisting of halo, aryl, heteroaryl,heterocyclyl, $R^{22}$, $SR^{20}$, $S(O)R^{21}$, $SO_2R^{21}$, $SO_2NR^{20}R^{23}$, $NR^{20}R^{23}$, $NR^{20}$, $COR^{21}$, $NR^{20}CO_2R^{21}$, $NR^{20}CONR^{20}R^{23}$, $NR^{20}SO_2R^{21}$, $OR^{20}$, CN, $CO_2R^{20}$, $CONR^{20}R^{23}$, and $COR_{20}$. In some compositions $R_4$ and $R_5$ are preferably each H, —$CH_2CH_2OH$, —$CHR'CH_2OH$, or —$CH_2CHR'OH$, —$CH_2CH_2NH_2$, $CHR'CH_2NH_2$, —$CH_2CHR'NH_2$ wherein R' is hydrogen or alkyl having from 1 to 6 carbon atoms.

$R^{20}$ is preferably a member selected from the group consisting of H, $C_{1-8}$ alkyl.

$R^{21}$ is preferably a member selected from the group consisting of $C_{1-3}$ alkyl, which alkyl is optionally substituted with 1 to 2 substituents independently selected from the group of halo, $CF_3$, CN, $OR^{20}$, $SR^{20}$, $N(R^{20})_2$.

$R^{22}$ is preferably a member selected from the group consisting of $C_{1-3}$ alkyl, aryl, heteroaryl which alkyl, aryl, and heteroaryl are optionally substituted with 1 to 3 substituents independently selected from halo, alkyl, mono- or dialkylamino, alkyl or aryl, CN, O—$C_{1-6}$ alkyl, and $CF_3$.

Preferred 2,6,9-trisubstituted purine compositions of this invention include:

2-{(2-hydroxyethyl)[9-(methylethyl)-6-({[4-(trifluoromethyl)phenyl]methyl}amino)purin-2-yl]amino}ethan-1-ol;
{((2S)oxolan-2-yl)methyl](6-{[(4-fluorophenyl)methyl]amino}-9-(methylethyl)purin-2-yl)amine,
[((2R)oxolan-2-yl)methyl](6-{[(4-fluorophenyl)methyl]amino}-9-(methylethyl)purin-2-yl)amine,
(2-aminoethyl)(6-{[3,5-dichlorophenyl)methyl]amino}-9-(methylethyl)purin-2-yl)amine,
(2-aminoethyl)[6-({[4-chloro-3-(trifluoromethyl)phenyl]methyl}amino)-9-(methylethyl)purin-2-yl]amine,
[-[(6-{[(4-chlorophenyl)methyl]amino}-9-(methylethyl)purin-2-yl)amino]-3-methylbutanamide,
(2-amino-2-methylpropyl)(6-{[(4-chlorophenyl)methyl]amino}-9-(methylethyl)purin-2-yl)amine,
3-(2-[bis(2-hydroxyethyl)amino]-6-{[4-chlorophenyl)methyl]amino}purin-9-yl)butan-2-one,
2-[(6-{[(4-chlorophenyl)methyl]amino}-9-(methylethyl)purin-2-yl)amino]-3-methylbutan-1-ol,
4-[({2-[(2-aminoethyl)amino]-9-(methylethyl)purin-6-yl}amino)methyl]benzenesulfonamide,
2-[(2-hydroxyethyl)(6-{[(4-methoxyphenyl)methyl]amino}-9-(methylethyl)purin-2-yl)amino]ethan-1-ol,
2-((2-hydroxyethyl){9-(methylethyl)-6-[(4-phenylphenyl)amino]purin-2-yl }amino)ethan-1-ol,
{2-[(2-amino-2-propyl)amino]-9-(methylethyl)purin-6-yl}[(4-chlorophenyl)methyl]amine,
{2-[(2-aminoethyl)amino]-9-(methylethyl)purin-6-yl}[(4-chlorophenyl)methyl]amine,
{2-[(2-aminopropyl)amino]-9-(methylethyl)purin-6-yl}[(4-chlorophenyl)methyl]amine, and
2-[(2-aminoethyl)(6-{[(4-chlorophenyl)methyl]amino}-9-(methylethyl)purin-2-yl)amino]ethan-1-ol.

There are some limitations to the scope of $R_1$, $R_1'$, $R_2$ and $R_3$. As mentioned above, when $R_3$ is 2-hydroxyethylamino and $R_2$ is methyl, $R_1'$—X cannot be amino, 3-methyl-2-butenylamino, benzylamino, or m-hydroxybenzyl-amino. When $R_3$ is 2-hydroxyethylamino and $R_2$ is isopropyl, $R_1'$—X cannot be benzylamino, m-hydroxybenzylamino, or 3-methylbutylamino. When $R_3$ is 2-hydroxyethylamino and $R_2$ is 2-hydroxyethyl, $R_1'$—X cannot be benzylamino. When $R_3$ is 2-propanol-2-methylamino or 2-dimethylaminoethylamino and $R_2$ is methyl, $R_1'$—X cannot be benzylamino.

The following are definitions for certain terms used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'" R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 14, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

"Pharmacologically acceptable salt"—a salt prepared by conventional means, and are well known by those skilled in the art. The "pharmacologically acceptable salts" include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of formula I-III include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of the types of compounds that are "pharmacologically acceptable salts," see Berge et al, *J. Pharm. Sci.* 66, 1 (1977).

If the final 2,6,9-trisubstituted purine compound of this invention contains a basic group, then an acid addition salt of the composition may be prepared. Acid addition salts of the compounds of this invention are prepared in a standard manner in a suitable solvent from the parent compound and an excess of acid, such as, but not limited to, hydrochloric, hydrobromic, sulfuric, phosphoric, acetic, maleic, succinic, citric or methanesulfonic. The hydrochloric salt form is especially useful.

If the final 2,6,9-trisubstituted purine compound contains an acidic group, then cationic salts of the composition may be prepared. Typically the acidic parent compound is treated with an excess of an alkaline reagent, such as, but not limited to, hydroxide, carbonate or alkoxide, containing the appropriate cation such as but not limited to, $Na^+$, $K^+$, $Ca^{+2}$ and $NH_4^+$. Certain of the compounds form inner salts or zwitterions, which are also acceptable.

The compounds of this invention are useful in inhibiting cell proliferation in mammals including humans. The 2,6,9-trisubstituted purines are useful in for example in treating autoimmune diseases, e.g. rheumatoid arthritis, lupus, type I diabetes, multiple sclerosis, cancer, cardiovascular disease such as restenosis following balloon angioplasty and atherectomy, restensosis following vascular modifying surgical procedures, host vs graft disease, gout, polycystic kidney disease and other proliferative diseases whose pathogenesis involves abnormal cell proliferation. In particular, the compositions of this invention are useful in treating cancers including cancers including lymphoyd neoplasm, cancer of the colon, breast cancer, ovarian cancer, pancreatic cancer, and cancers derived of endotherical cells.

The method of treatment comprises the administration parenterally, and orally, of an effective quantity of the chosen compound of this invention, preferably dispersed in a pharmaceutical carrier. Therapeutically useful amounts of the composition of this invention will generally range from about 0.01 to about 100 mg/kg, but will be readily determined by one skilled in the art depending upon the route of administration, and the age and condition of the patient. Therapeutically useful amounts of the composition of this invention may be administered from one to ten times daily or more for acute or chronic disease. No unacceptable toxicological effects are expected when compounds of the invention are administered in accordance with the present invention.

The compounds of this invention are also useful as antiinflammatory and antifungal agents. As such, the compositions of this invention are useful for treating antiinflammatory and fungal infections in humans, animals, and fungal infections in plants.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration.

It may be desirable to add excipients such as polyvinylpyrrolidinone, gelatin, hydroxycellulose, acaia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include, but are not limited to syrup, peanut oil, olive oil, glycerin, saline, alcohols, and water. Solid carriers include, but are not limited to, starch, lactose, calcium sulfate, dihydrate, teffa alba, magnesium stearate or stearic acid, talc, pectin, acacia, agar or gelatin. The carrier may also include a sustained release material such as, but not limited to, glyceryl monostearate or glyceryl distearate, alone or with a wax. The amount of solid carrier varies but, preferably, will be between about 20 mg to about 1 gram per dosage unit.

The pharmaceutical dosages are made using conventional techniques such as, but not limited to, milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples that follow serve to illustrate this invention. The Examples are intended to in no way limit the scope of this invention, but are provided to show how to make and use the compounds of this invention. In the Examples, all temperatures are in degrees Centigrade. RT indicates room temperature.

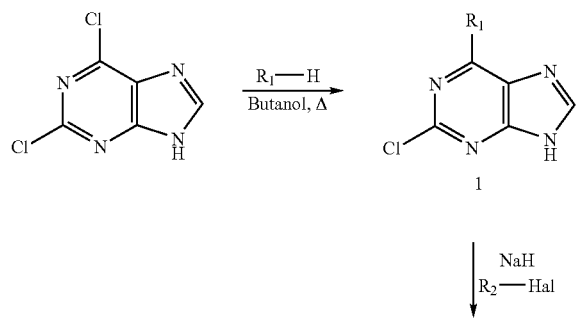

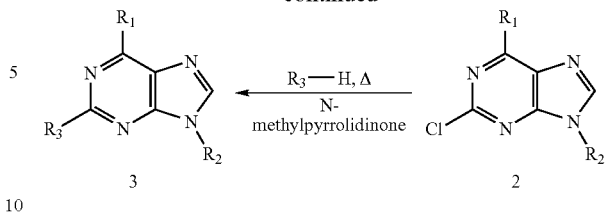

EXAMPLE 1

The compounds of this invention are prepared by conventional methods of organic chemistry. The reaction sequence outlined in the synthesis scheme below is a general method useful for the synthesis of compounds of this invention. 2,6-dichloropurine is dissolved in butanol and the appropriate $R_1$ amine is added. After heating for several hours, the reaction mixture is cooled, and the compound 1 is obtained. To compound 1, is added, sodium hydride followed by $R_2$, and compound 2 is isolated. To compound 2, $R_3$ is added in solution with N-methylpyrrolidinone. The mixture is heated for an appropriate period followed by purification leading to the desired compound.

The following compound was prepared according to the method above.

Preparation of
2-chloro-6-(4-methoxybenzylamino)purine (1)

The 2,6-dichloropurine (4.06 g, 21.5 mmol) was suspended in n-butanol (150 ml) and the 4-methoxybenzylamine was added (3.4 ml, 26 mmol). The solution turned clear and then cloudy a few minutes later. The solution was heated at 120° C. for 2 hr and then cooled. The n-butanol was evaporated followed by suspension of the residue in water and diethyl ether mixture. A solution of 2N NaOH (1.3 ml, 26 mmol) was added and the solution stirred for 10 min before filtration. The filtered precipitate was washed with water and a small portion of ether and then dried under vacuum. The residual liquor was left overnight and more crystals were collected the next day and washed with diethyl ether.

Preparation of 2-chloro-6-(4-methoxybenzylamino)-
9-isopropylpurine (2)

2-chloro-6-(4-methoxybenzylamino)purine was suspended in dry DMF (5 ml) and treated with sodium hydride, 60% dispersion (82 mg, 2.06 mmol). The suspension was stirred for 30 min over which time it became a clear yellow/green solution. 2-Iodopropane (0.280 mL, 1.7 eq.) was added over 5 min and the resultant solution stirred for 2 days. Water was added and the solution and extracted with ethyl acetate. The organic layer was evaporated to give the product isopropyl purine.

Preparation of 2-diethanolamino-6-(4-methoxybenzylamino)-9-isopropylpurine, (3)

The purine (1.65 g, 4.98 mmol) was dissolved in DMSO (12 mL) and diethanolamine (4 mL) and then heated at 140°

C. for 2–3 days and then at 160° C. for 1 day. The solution was cooled and water saturated butanol was added (100 mL). The solution was then washed with water (3×50 mL), before being evaporated to give brown oil. The residue was chromatographed over silica gel eluting with ethyl acetate, followed by 3% methanol in ethyl acetate to give the product. $^1$H-NMR($\delta$ CDCl3): 7.29(br s 1H), 7.25(d, 2H), 6.94(br s. 1H), 6.83(d. 2H), 5.43(br s.<2H), 4.63(br s. 2H), 4.53(m 1H), 3.86(t. 4H), 3.76(m, 7H), 1.47(d 6H).

Table 1 identifies compounds of this invention that were prepared according to the synthesis method set forth in this Example.

TABLE 1

COMPOUNDS PREPARED BY THE METHOD OF EXAMPLE 1

| $R_1$ | $R_2$ | $R_3$ |
|---|---|---|
| (4-methoxyphenyl)methylamino | 3-cyanopropyl | Cl |
| (4-methoxyphenyl)methylamino | 3-chloropropyl | Cl |
| (4-methoxyphenyl)methylamino | Benzyl | Cl |
| (4-methoxyphenyl)methylamino | (4-methylcarboxyphenyl)methyl | Cl |
| (4-methoxyphenyl)methylamino | 2-(N-phtyhaloyl)ethyl | Cl |
| (4-methoxyphenyl)methylamino | Isopropyl | Ethanolamine |
| (4-methoxyphenyl)methylamino | Isopropyl | Diethanolamine |
| (4-methoxyphenyl)methylamino | 3-methylbutyl | Cl |
| (4-methoxyphenyl)methylamino | 2-methylbutyl | Cl |
| (4-methoxyphenyl)methylamino | Cyclopentyl | Cl |
| (4-methoxyphenyl)methylamino | (3-nitrophenyl)methyl | Cl |
| (4-methoxyphenyl)methylamino | (4-nitrophenyl)methyl | Cl |
| (4-methoxyphenyl)methylamino | Ethyl | Cl |
| (4-methoxyphenyl)methylamino | Propyl | Cl |
| (4-methoxyphenyl)methylamino | (3-methylphenyl)methyl | Cl |
| (4-methoxyphenyl)methylamino | (4-methylphenyl)methyl | Cl |
| Heptylamino | H | Cl |
| N-benzyl-N-hydroxylamino | H | Cl |
| Propylamino | H | Cl |
| Noradamantylamino | H | Cl |
| Cyclobutylamino | H | Cl |
| 3-methoxypropylamino | H | Cl |
| 2-methoxyethylamino | H | Cl |
| Cyclopentylamino | H | Cl |
| 1-hydroxy-2-methyl-2-propylamino | H | Cl |
| (N-1-benzylpiperidinyl)-4-amino | H | Cl |
| Heptylamino | Methyl | Cl |
| N-benzyl-N-hydroxylamino | Methyl | Cl |
| Propylamino | Methyl | Cl |
| Noradamantylamino | Methyl | Cl |
| Cyclobutylamino | Methyl | Cl |
| 3-methoxypropylamino | Methyl | Cl |
| 2-methoxyethylamino | Methyl | Cl |
| Cyclopentylamino | Methyl | Cl |
| 1-hydroxy-2-methyl-2-propylamino | Methyl | Cl |
| (N-1-benzylpiperidinyl)-4-amino | Methyl | Cl |
| (2,4-dimethoxyphenyl)methylamino | Methyl | Cl |
| (2-methoxyphenyl)methylamino | H | Cl |
| (2-pryidinyl)methylamino | H | Cl |
| (3,4-dimethoxyphenyl)ethylamino | H | Cl |
| (3-pyridinyl)methylamino | H | Cl |
| (4-pyridinyl)methylamino | H | Cl |
| 6-hydroxy-1-hexylamino | H | Cl |
| Phenethylamino | H | Cl |
| (2-benzothiazolyl)amino | H | Cl |
| (2,4-dimethoxyphenyl)methyalmino | H | Cl |
| (2-methoxyphenyl)methylamino | Methyl | Cl |
| (2-pyridinyl)methylamino | Methyl | Cl |
| (3,4-dimethoxyphenyl)ethylamino | Methyl | Cl |
| (4-methoxyphenyl)methylamino | Methyl | Cl |
| (3-pyridinyl)methylamino | Isopropyl | 2-aminoethylamino |
| (4-pyridinyl)methylamino | H | Cl |
| 1-hydroxy-6-hexylamino | H | Cl |
| Phenethylamino | H | Cl |
| (2-benzothiazolyl)amino | H | Cl |
| (4-methoxyphenyl)methylamino | H | Cl |
| 3-phenyl-1-propylamino | Isopropyl | 3-hydroxypyrrolidino |
| (2-indanyl)amino | H | Cl |
| (4-methoxyphenyl)ethylamino | H | Cl |
| (4-nitrophenyl)methylamino | H | Cl |
| (2,6-difluorophenyl)methylamino | H | Cl |
| 3-phenyl-1-propylamino | H | Cl |
| (2-indanyl)amino | Methyl | Cl |
| (4-methoxyphenyl)ethylamino | Methyl | Cl |
| (4-nitrophenyl)methylamino | Methyl | Cl |
| (2,6-difluorophenyl)methylamino | Methyl | Cl |

TABLE 1-continued

COMPOUNDS PREPARED BY THE METHOD OF EXAMPLE 1

| R₁ | R₂ | R₃ |
| --- | --- | --- |
| Cyclopropylmethylamino | Methyl | Cl |
| 4-(1,2-methylenedioxyphenyl)methylamino | H | Cl |
| (4-aminosulfonylphenyl)methylamino | H | Cl |
| (Cyclohexanol)-1-methylamino | H | Cl |
| (2-benzimidazoly)methylamino | H | Cl |
| Cyclohexylmethylamino | H | Cl |
| (4-methoxyphenyl)methylamino | H | Cl |
| (4-methoxyphenyl)methylamino | Isopropyl | (2-hydroxy-1-hydroxymethyl)ethylamino |
| Cyclopropylmethylamino | Isopropyl | 3-amino-2-hydroxypropylamino |
| 4-(1,2-methylene-dioxyphenyl)methylamino | Methyl | Cl |
| (4-aminosulfonyl-phenyl)methylamino | Methyl | Cl |
| (Cyclohexanol)-1-methylamino | Methyl | Cl |
| (2-benzimidazolyl)methylamino | Methyl | Cl |
| Cyclohexylmethylamino | Methyl | Cl |
| (3-pyridinyl)methylamino | Methyl | Cl |
| (4-pyridinyl)methylamino | 2-methylpropyl | Cl |
| 6-hydroxyhexylamino | Cyclopentyl | Cl |
| Phenethylamino | Propyl | Cl |
| (2-benzothiazolyl)amino | Ethyl | Cl |
| 3-phenyl-1-propylamino | Isopropyl | Cl |
| (2-indanyl)amino | 2-methylpropyl | Cl |
| 2-(4-methoxyphenyl)ethylamino | Cyclopentyl | Cl |
| (4-nitrophenyl)methylamino | Propyl | Cl |
| (2,6-difluorophenyl)methylamino | Ethyl | Cl |
| (4-methoxyphenyl)methylamino | Isopropyl | Cl |
| 3-phenyl-1-propylamino | Isopropyl | 4-hydroxypiperidino |
| (2-indanyl)amino | H | Cl |
| 2-(4-methoxyphenyl)ethylamino | H | Cl |
| (4-nitrophenyl)methylamimo | H | Cl |
| (2,6-difluorophenyl)methylamino | H | Cl |
| (4-methoxyphenyl)methylamino | H | Cl |
| (4-methoxyphenyl)methylamino | Isopropyl | N-(2-cyanoethyl)-N-benzylamino |
| 3-phyenyl-1-propylamino | Isopropyl | 1-(r,s)-hydroxymethyl-3-methylbutylamino |
| (2-indanyl)amino | Isopropyl | Cl |
| 2-(4-methoxyphenyl)ethylamino | Isopropyl | Cl |
| (4-nitrophenyl)methylamino | Isopropyl | Cl |
| (2,6-difluorophenyl)methylamino | Isopropyl | Cl |
| (4-methoxyphenyl)methylamino | Isopropyl | Cl |
| (4-methoxyphenyl)methylamino | Isopropyl | Piperidino |
| (4-methoxyphenyl)methylamino | Isopropyl | 3-hydroxypiperidino |
| 3-phenyl-1-propylamino | Isopropyl | 1-(s)-hydroxymethyl-2-(4'-imidazolyl)ethylamino |
| (2-indanyl)amino | Isopropyl | Diethanolamino |
| (4-methyoxyphenyl)methylamino | Isopropyl | Diethanolamino |
| (4-methyoxyphenyl)methylamino | Isopropyl | 2-(s)-hydroxymethylpyrrolidino |
| (4-methyoxyphenyl)methylamino | Isopropyl | Diethanolamino |
| (4-methyoxyphenyl)methylamino | Benzyl | Morpholino |
| (4-methyoxyphenyl)methylamino | 3-methylbutyl | Diethanolamino |
| (4-methyoxyphenyl)methylamino | 2-methylbutyl | Diethanolamino |
| (4-methyoxyphenyl)methylamino | Cyclopentyl | Diethanolamino |
| (4-methyoxyphenyl)methylamino | (3-nitrophenyl)methylamino | Diethanolamino |
| (4-methyoxyphenyl)methylamino | (4-nitrophenyl)methylamino | Diethanolamino |
| (4-methyoxyphenyl)methylamino | Ethyl | Diethanolamino |
| (4-methyoxyphenyl)methylamino | Propyl | Diethanolamino |
| (4-methyoxyphenyl)methylamino | (3-methylphenyl)methylamino | Diethanolamino |
| Heptylamino | (4-methylphenyl)methylamino | Diethanolamino |
| N-benzyl-N-hydroxyamino | Methyl | Diethanolamino |
| Propylamino | Methyl | Diethanolamino |
| Noradamantylamino | Methyl | Diethanolamino |
| Cyclobutylamino | Methyl | Diethanolamino |
| 3-methoxypropylamino | Methyl | Diethanolamino |
| 2-methoxyethylamino | Methyl | Diethanolamino |
| Cyclopentylamino | Methyl | Diethanolamino |
| 1-hydroxy-2-methyl-2-propylamino | Methyl | Diethanolamino |
| 4-(1-benzylpiperidinyl)amino | Methyl | Diethanolamino |
| (4-methoxyphenyl)methylamino | Methyl | Diethanolamino |
| (4-methoxyphenyl)methylamino | Isopropyl | Diethanolamino |
| (2,4-dimethoxy-phenyl)methylamino | Isopropyl | 3-hydroxypyrrolidino |

TABLE 1-continued

COMPOUNDS PREPARED BY THE METHOD OF EXAMPLE 1

| $R_1$ | $R_2$ | $R_3$ |
|---|---|---|
| (2-methoxyphenyl)methylamino | Methyl | 2-(3'indolyl)ethylamino |
| (2-pyridinyl)methylamino | Methyl | Diethanolamino |
| 2-(3,4-dimethoxyphenyl)ethylamino | Methyl | Diethanolamino |
| (3-pyridinyl)methylamino | Methyl | Diethanolamino |
| (4-pyridinyl)methylamino | Methyl | Diethanolamino |
| 6-hydroxy-1-hexylamino | Methyl | Diethanolamino |
| Phenethylamino | Methyl | Diethanolamino |
| (2-benzothiazolyl)amino | Methyl | Diethanolamino |
| 3-phenyl-1-propylamino | Methyl | Diethanolamino |
| (2-indanyl)amino | Methyl | Diethanolamino |
| 2-(4-methoxyphenyl)ethylamino | Methyl | Diethanolamino |
| (4-nitrophenyl)methylamino | Methyl | Diethanolamino |
| (2,6-difluorophenyl)methylamino | Methyl | Diethanolamino |
| Cyclopropylmethylamino | Methyl | Diethanolamino |
| 4-(1,2-methylenedioxy-phenyl)methylamino | Methyl | Diethanolamino |
| (4-aminosulfonylphenyl)-methylamino | Methyl | Diethanolamino |
| (Cyclohexanol)-1-methylamino | Methyl | Diethanolamino |
| (2-benzimidazolyl)methylamino | Methyl | Diethanolamino |
| Cyclohexylmethylamino | Methyl | Diethanolamino |
| (3-pyridyl)methylamino | Methyl | Diethanolamino |
| (4-pyridyl)methylamino | 2-methylpropyl | Diethanolamino |
| 6-hydroxy-1-hexylamino | Cyclopentyl | Diethanolamino |
| 2-phenethylamino | Propyl | Diethanolamino |
| (2-benzothiazolyl)amino | Ethyl | Diethanolamino |
| 3-phenyl-1-propylamino | Isopropyl | Diethanolamino |
| (2-indanyl)amino | 2-methylpropyl | Diethanolamino |
| 2-(4-methoxyphenyl)ethylamino | Cyclopentyl | Diethanolamino |
| (4-nitrophenyl)methylamino | Propyl | Diethanolamino |
| (2,6-difluorophenyl)methylamino | Ethyl | Diethanolamino |
| (4-methyoxyphenyl)methylamino | Isopropyl | Diethanolamino |
| (4-methyoxyphenyl)methylamino | Isopropyl | 1-hydroxymethyl cyclopentylamino |
| (4-methyoxyphenyl)methylamino | Isopropyl | 2-(R,S)-hydroxymethylpiperidino |
| Cyclopropylmethylamino | Isopropyl | 2,3-dihydroxy-1-propylamino |
| 4-(1,2-methylenedioxyphenyl)methylamino | Isopropyl | Cl |
| (4-aminosulfonylphenyl)methylamino | Isopropyl | Cl |
| (Cyclohexanol)-1-methylamino | Isopropyl | Cl |
| (2-benzimidazolyl)amino | Isopropyl | Cl |
| Cyclohexylmethylamino | Isopropyl | Cl |
| 3-phenyl-1-propylamino | Isopropyl | Cl |
| Cyclopropylmethylamino | Cyclopentyl | Cl |
| 4-(1,2-methylenedioxyphenyl)methylamino | Isopropyl | Diethanolamino |
| (4-methoxyphenyl)methylamino | Isopropyl | Diethanolamino |
| (4-methoxyphenyl)methylamino | Isopropyl | Diisopropylamino |
| (4-methoxyphenyl)methylamino | Isopropyl | (Trans-2-hydroxycyclohexyl)amino |
| (4-methoxyphenyl)methylamino | Isopropyl | 2(R)-(1-hydroxy-3-phenyl)propylamino |
| (4-methoxyphenyl)methylamino | Isopropyl | 5-(S)-(2,2-dimethyl-4(s)-phenyldioxalanyl)amino |
| (4-methoxyphenyl)methylamino | Isopropyl | 3-(N-1-imidazolyl)propylamino |
| (4-methoxyphenyl)methylamino | Isopropyl | 4-hydroxyl-4-phenylpiperidino |
| (4-methoxyphenyl)methylamino | Isopropyl | (2-benzylthio-1-hydroxymethyl)ethylamino |
| (4-methoxyphenyl)methylamino | Isopropyl | N-methyl-N-(2-hydroxy-2-(3,4-dihydroxyphenyl)ethyl)amino |
| (4-methoxyphenyl)methylamino | Isopropyl | Diallylamino |
| (4-methoxyphenyl)methylamino | Isopropyl | Piperazino |
| (4-methoxyphenyl)methylamino | Isopropyl | (+/−)N-methyl-N-(2-hydroxy-2-phenylethyl)amino |
| (4-methoxyphenyl)methylamino | Isopropyl | (S)-(+)-2-(anilinomethyl)pyrrolidino |
| (4-methoxyphenyl)methylamino | Isopropyl | (+/−)N-(2-propenyl)-N-2-(4-hydroxy-2-methylpentyl)amino |
| (4-methoxyphenyl)methylamino | Isopropyl | N-(2-hydroxyethyl)-N-(3-hydroxypropyl)amino |
| (4-methoxyphenyl)methylamino | Isopropyl | Di-N-1-(2-hydroxy-2-methylpentyl)amino |

TABLE 1-continued

COMPOUNDS PREPARED BY THE METHOD OF EXAMPLE 1

| $R_1$ | $R_2$ | $R_3$ |
|---|---|---|
| (4-methoxyphenyl)methylamino | Isopropyl | Di-N-2-(3-hydroxybutyl)amino |

EXAMPLE 2

This example describes a method for preparing compounds of this invention according to the following general synthesis scheme:

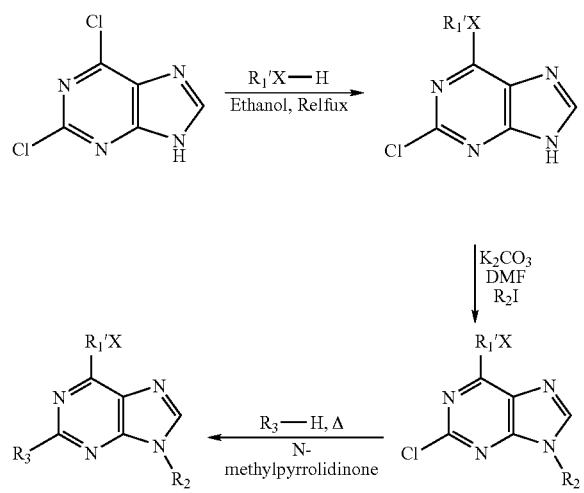

Preparation of {2-chloropurin-6-yl}[(4-chlorophenyl)methyl]amine

To a suspension of 15 g (0.0794 mol) of 2,6-dichloropurine in 250 mL of absolute ethanol was added 12.7 mL (0.0873 mol) of triethylamine and 10.62 mL (0.0873 mol) of 4-chlorobenzylamine. The mixture was refluxed at 80° C. for 16 h (the formation of creamy white precipitate was observed). The reaction mixture was cooled and the precipitated product was removed by filtration. The precipitate was washed with ethanol (350 mL) and dried in high vacuum for 24 h. Product was characterized by $^1$H-NMR.

Preparation of {2-chloro-9-(methylethyl)purin-6-yl}[4-chlorophenyl)methyl]amine

To a solution of 6 g (0.020 mol) of 2-chloro-6-(4-chlorophenyl)methylaminopurine in 41 mL of anhydrous DMF was added 5.64 g (0.041 mol) anhydrous potassium carbonate and 3.41 mL,(0.035 mol of 2-iodopropane) and stirred at room temperature for 16 h. To the mixture 500 mL of water was added and stirred for 1 h. The precipitate was filtered, washed with water (350 mL), and dried in vacuum oven at 50° C. for 16 h. The product was obtained as an off white solid and characterized by $^1$H-NMR.

Preparation of {2-[(2-aminoethyl)amino]-9-(methylethyl)purin-6-yl}[(4-chlorophenyl)methyl]amine To a solution of 3.36 g (0.01 mol) of {2-chloro-9-(methylethyl)purin-6-yl}[4-chlorophenyl)methyl]amine in 13 mL of anhy. 1-methyl-2-pyrrolidinone was added 4.68 mL (0.70 mol) of 2-aminoethylamine and the mixture was heated at 140° C. for 24 h. The compound was subjected to variable gradient chromatography on silica gel with dichloromethane/methanol mixtures and yielded 1-methyl-2-pyrrolidinone. The mixture was dissolved in dichloromethane and extracted with water (520 mL). The organic layer was dried over anhydrous. Sodium sulfate and evaporated to an off white solid. The product was characterized by $^1$H-NMR and purity checked by RP-HPLC (YMC C-18 column; 50×4.4 mm; S-5 120 A° 0.1% TFA-water/0.1% TFA-acetonitrile).

Table 2, below identifies compounds of this invention that were prepared according to the general synthesis method set forth in this Example. In Table 2, MS=Mass Spectrum and MH+=mass of parent molecular ion plus one hydrogen atom.

TABLE 2

COMPOUNDS PREPARED BY THE METHOD OF EXAMPLE 2

| $R_1$ | $R_2$ | $R_3$ | MS(MH+) |
|---|---|---|---|
| (4-Methylphenyl)methylamino | Isopropyl | 2-Aminoethylamino | 340 |
| (2,4-Dichlorophenyl)methylamino | Isopropyl | Diethanolamino | 439 |
| (2,4-Dichlorophenyl)methylamino | Isopropyl | 2-Aminoethylamino | 394 |
| (3-Methylphenyl)methylamino | Isopropyl | Diethanolamino | 385 |
| (3-Methylphenyl)methylamino | Isopropyl | 2-Aminoethylamino | 340 |
| (3-Methylphenyl)methylamino | Isopropyl | 2-(N2-Dimethylamino)-N1-benzylethylamino | 458 |
| (4-Trifluoromethylphenyl methylamino | Isopropyl | 2-Aminoethylamino | 394 |
| (4-Trifluoromethylphenyl)methylamino | Isopropyl | 1-Hydroxymethyl-2-methylpropylamino | 437 |
| (3,5-Bis-trifluoromethylphenyl)methylamino | Isopropyl | Diethanolamino | 507 |
| (3,5-Bis-trifluoromethylphenyl)methylamino | Isopropyl | 2-Aminoethylamino | 462 |

TABLE 2-continued

COMPOUNDS PREPARED BY THE METHOD OF EXAMPLE 2

| $R_1$ | $R_2$ | $R_3$ | MS(MH+) |
|---|---|---|---|
| (3,5-Bis-trifluoromethylphenyl)methylamino | Isopropyl | 1-Hydroxymethyl-2-methylpropylamino | 505 |
| (3-Chlorophenyl)methylamino | Isopropyl | 1-Hydroxymethyl ethylamino | 375 |
| (2-Trifluoromethyl-phenyl)methylamino | Isopropyl | 1-Hydroxymethyl ethylamino | 409 |
| (4-Chloro-3-trifluoromethyl-phenyl)methylamino | Isopropyl | 1-Hydroxymethyl ethylamino | 443 |
| (3-Chlorophenyl)methylamino | Isopropyl | 2-Hydroxyethylamino | 361 |
| (2-Trifluromethyl-phenyl)methylamino | Isopropyl | 2-Hydroxyethylamino | 395 |
| (4-Chloro-3-trifluoromethyl-phenyl)methylamino | Isopropyl | 2-Hydroxyethylamino | 429 |
| (3-Chlorophenyl)methylamino | Isopropyl | (1R,2S)-2-Hydroxy-1-methyl-2-phenylethylamino | 451 |
| (2-Chlorophenyl)methylamino | Isopropyl | Diethanolamino | 450 |
| (2,5-Difluorophenyl)methylamino | Isopropyl | Diethanolamino | 407 |
| (1-Naphthyl)methylamino | Isopropyl | Diethanolamino | 421 |
| (2-Chlorophenyl)methylamino | Isopropyl | 2-Aminoethylamino | 360 |
| (2,5-Difluorophenyl)methylamino | Isopropyl | 2-Aminoethylamino | 362 |
| (1-Naphthyl)methylamino | Isopropyl | 2-Aminoethylamino | 376 |
| (2-Chlorophenyl)methylamino | Isopropyl | 1-Hydroxymethyl-2-methylethylamino | 403 |
| (2,5-Difluorophenyl)methylamino | Isopropyl | 1-Hydroxymethyl-2-methylethylamino | 405 |
| (1-Naphthyl)methylamino | Isopropyl | 1-Hydroxymethyl-2-methylethylamino | 419 |
| (3-Methylphenyl)methylamino | Isopropyl | 2-Aminopropylamino | 354 |
| (2-Chlorophenyl)methylamino | Isopropyl | 2-Aminopropylamino | 374 |
| (3-Chlorophenyl)methylamino | Isopropyl | 2-Aminopropylamino | 374 |
| (2,5-Difluorophenyl)methylamino | Isopropyl | 2-Aminopropylamino | 376 |
| (1-Naphthyl)methylamino | Isopropyl | 2-Aminopropylamino | 390 |
| (2-Chloro-5-trifluoromethylphenyl)methylamino | Isopropyl | Diethanolamino | 473 |
| (3-Chlorophenyl)methylamino | Isopropyl | 1-Hydroxymethyl-2-methylpropylamino | 403 |
| (2-Trifluoromethylphenyl methylamino | Isopropyl | 1-Hydroxymethyl-2-methylpropylamino | 437 |
| (3-Methylphenyl)methylamino | Isopropyl | 2-(2-Hydroxyethylamino)-ethylamino | 384 |
| (2-Chlorophenyl)methylamino | Isopropyl | 2-(2-Hydroxyethylamino)-ethylamino | 404 |
| (3-Chlorophenyl)methylamino | Isopropyl | 2-(2-Hydroxyethylamino)-ethylamino | 404 |
| (2,5-Difluorophenyl)methylamino | Isopropyl | 2-(2-Hydroxyethylamino)-ethylamino | 406 |
| (1-Naphthyl)methylamino | Isopropyl | 2-(2-Hydroxyethylamino)-ethylamino | 420 |
| (3,5-Bistrifluoromethyl-phenyl)methylamino | Isopropyl | 2-(2-Hydroxyethylamino)-ethylamino | 506 |
| (4-Isopropylphenyl)methylamino | Isopropyl | 2-(2-Hydroxyethylamino)-ethylamino | 412 |
| (2-Trifluoromethylphenyl)methylamino | Isopropyl | 2-(2-Hydroxyethylamino)-ethylamino | 438 |
| (4-Methylphenyl)methylamino | Isopropyl | 2-(2-Hydroxyethylamino)-ethylamino | 384 |
| (4-Chloro-3-trifluoromethylphenyl)methylamino | Isopropyl | 2-(2-Hydroxyethylamino)-ethylamino | 472 |
| (2-Chloro-5-trifluoromethylphenyl)methylamino | Isopropyl | 2-(2-Hydroxyethylamino)-ethylamino | 472 |
| (3,5-Dichlorophenyl)methylamino | Isopropyl | 2-(2-Hydroxyethylamino)-ethylamino | 438 |
| (1R)-(4-Methylphenyl)ethylamino | Isopropyl | 2-(2-Hydroxyethylamino)-ethylamino | 398 |
| (1R)-(2-Naphthyl)ethylamino | Isopropyl | 2-(2-Hydroxyethylamino)-ethylamino | 434 |
| (2,4-Dichloro-6-methylphenyl)methylamino | Isopropyl | 2-(2-Hydroxyethylamino)-ethylamino | 452 |
| (4-Trifluoromethylphenyl)methylamino | Isopropyl | 2-(2-Hydroxyethylamino)-ethylamino | 438 |
| (3-Methylphenyl)methylamino | Isopropyl | 2-Hydroxy-1-(S)-methylethylamino | 355 |
| (2-Chlorophenyl)methylamino | Isopropyl | 2-Hydroxy-1-(S)-methylethylamino | 375 |
| (2,5-Difluorophenyl)methylamino | Isopropyl | 2-Hydroxy-1-(S)-methylethylamino | 377 |
| (1-Naphthyl)methylamino | Isopropyl | 2-Hydroxy-1-(S)-methylethylamino | 391 |
| (3,5-Bistrifluoromethyl-phenyl)methylamino | Isopropyl | 2-Hydroxy-1-(S)-methylethylamino | 477 |
| (4-Isopropylphenyl)methylamino | Isopropyl | 2-Hydroxy-1-(S)-methylethylamino | 383 |
| (4-Methylphenyl)methylamino | Isopropyl | 2-Hydroxy-1-(S)-methylethylamino | 355 |

TABLE 2-continued

COMPOUNDS PREPARED BY THE METHOD OF EXAMPLE 2

| R₁ | R₂ | R₃ | MS(MH+) |
|---|---|---|---|
| (2-Chloro-5-trifluoromethylphenyl)methylamino | Isopropyl | 2-Hydroxy-1-(S)-methylethylamino | 443 |
| (5-Fluoro-2-trifluoromethylphenyl)methylamino | Isopropyl | 2-Hydroxy-1-(S)-methylethylamino | 427 |
| (3,5-Dichlorophenyl)methylamino | Isopropyl | 2-Hydroxy-1-(S)-methylethylamino | 409 |
| [R]-1-(4-Methylphenyl)ethylamino | Isopropyl | 2-Hydroxy-1-(S)-methylethylamino | 369 |
| [R]-1-(2-Naphthyl)ethylamino | Isopropyl | 2-Hydroxy-1-(S)-methylethylamino | 405 |
| (2,4-Dichlorophenyl)methylamino | Isopropyl | 2-Hydroxy-1-(S)-methylethylamino | 409 |
| (2,4-Dichloro-6-methylphenyl)methylamino | Isopropyl | 2-Hydroxy-1-(S)-methylethylamino | 423 |
| (4-Trifluoromethylphenyl)methylamino | Isopropyl | 2-Hydroxy-1-(S)-methylethylamino | 409 |
| (3-Methylphenyl)methylamino | Isopropyl | 2-Hydroxyethylamino | 341 |
| (2-Chlorophenyl)methylamino | Isopropyl | 2-Hydroxyethylamino | 361 |
| (2,5-Difluorophenyl)methylamino | Isopropyl | 2-Hydroxyethylamino | 363 |
| (1-Naphthyl)methylamino | Isopropyl | 2-Hydroxyethylamino | 377 |
| (3,5-Bistrifluoromethyl-phenyl)methylamino | Isopropyl | 2-Hydroxyethylamino | 463 |
| (4-Isopropylphenyl)methylamino | Isopropyl | 2-Hydroxyethylamino | 369 |
| (4-Methylphenyl)methylamino | Isopropyl | 2-Hydroxyethylamino | 341 |
| (2-Chloro-5-trifluoromethylphenyl)methylamino | Isopropyl | 2-Hydroxyethylamino | 429 |
| (5-Fluoro-2-trifluoromethylphenyl)methylamino | Isopropyl | 2-Hydroxyethylamino | 413 |
| (3,5-Dichlorophenyl)methylamino | Isopropyl | 2-Hydroxyethylamino | 395 |
| (1R)-(4-Methylphenyl)ethylamino | Isopropyl | 2-Hydroxyethylamino | 355 |
| (1R)-(2-Naphthyl)ethylamino | Isopropyl | 2-Hydroxyethylamino | 391 |
| (2,4-Dichlorophenyl)methylamino | Isopropyl | 2-Hydroxyethylamino | 395 |
| (2,4-Dichloro-6-methylphenyl)methylamino | Isopropyl | 2-Hydroxyethylamino | 409 |
| (4-Trifluoromethylphenyl)methylamino | Isopropyl | 2-Hydroxyethylamino | 395 |
| (3-Methylphenyl)methylamino | Isopropyl | 1-Hydroxymethyl propylamino | 369 |
| (2-Chlorophenyl)methylamino | Isopropyl | 1-Hydroxymethyl propylamino | 389 |
| (3-Chlorophenyl)methylamino | Isopropyl | 1-Hydroxymethyl propylamino | 389 |
| (2,5-Difluorophenyl)methylamino | Isopropyl | 1-Hydroxymethyl propylamino | 391 |
| (1-Naphthyl)methylamino | Isopropyl | 1-Hydroxymethyl propylamino | 405 |
| (3,5-Bistrifluoromethyl-phenyl)methylamino | Isopropyl | 1-Hydroxymethyl propylamino | 491 |
| (4-Isopropylphenyl)methylamino | Isopropyl | 1-Hydroxymethyl propylamino | 397 |
| (2-Trifluoromethylphenyl)methylamino | Isopropyl | 1-Hydroxymethyl propylamino | 423 |
| (4-Methylphenyl)methylamino | Isopropyl | 1-Hydroxymethyl propylamino | 369 |
| (4-Chloro-3-trifluoromethylphenyl)methylamino | Isopropyl | 1-Hydroxymethyl propylamino | 457 |
| (2-Chloro-5-trifluoromethylphenyl)methylamino | Isopropyl | 1-Hydroxymethyl propylamino | 457 |
| (5-Fluoro-2-trifluoromethylphenyl)methylamino | | 1-Hydroxymethyl propylamino | 441 |
| (3,5-Dichlorophenyl)methylamino | Isopropyl | 1-Hydroxymethyl propylamino | 423 |
| (1R)-(4-Methylphenyl)ethylamino | Isopropyl | 1-Hydroxymethyl propylamino | 383 |
| (1R)-(2-Naphthyl)ethylamino | Isopropyl | 1-Hydroxymethyl propylamino | 419 |
| (2,4-Dichlorophenyl)methylamino | Isopropyl | 1-Hydroxymethyl propylamino | 423 |
| (2,4-Dichloro-6-methylphenyl)methylamino | Isopropyl | 1-Hydroxymethyl propylamino | 437 |
| (4-Trifluoromethylphenyl)methylamino | Isopropyl | 1-Hydroxymethyl propylamino | 423 |
| (3,5-Dichlorophenyl)methylamino | Isopropyl | 2-(2-Hydroxyethylamino)-ethylamino | 438 |
| (3,5-Dichlorophenyl)methylamino | Isopropyl | (2S)-pyrrolomethylamino | 434 |
| (4-Chlorophenyl)methylamino | Isopropyl | 2-Aminocyclohexylamino | 414 |
| (4-Chlorophenyl)methylamino | Isopropyl | 3-Aminocyclohexylamino | 414 |
| (3-Fluoro-6-trifluoromethyl-phenyl)methylamino | Isopropyl | Diethanolamino | 457 |
| (2-Chloro-5-trifluoromethyl-phenyl)methylamino | Isopropyl | 2-Aminoethylamino | 428 |
| (3,5-Bis-trifluoromethyl-phenyl)methylamino | Isopropyl | 2-Aminopropylamino | 476 |
| (2-Trifluoromethyl-phenyl)methylamino | Isopropyl | 2-Aminopropylamino | 408 |
| (4-methylphenyl)methylamino | Isopropyl | 2-Aminopropylamino | 354 |
| (4-Chloro-3-trifluoromethyl-phenyl)methylamino | Isopropyl | 2-Aminopropylamino | 442 |
| (2-Chloro-5-trifluoromethyl-phenyl)methylamino | Isopropyl | 2-Aminopropylamino | 442 |
| [R]-1-(4-methylphenyl)ethylamino | Isopropyl | 2-aminoethylamino | 354 |
| [R]-1-(2-Naphthyl)ethylamino | Isopropyl | 2-Aminoethylamino | 390 |
| (2-Chloro-5-trifluoromethyl-phenyl)methylamino | Isopropyl | 1-Hydroxymethyl-2-methylpropylamino | 471 |

TABLE 2-continued

COMPOUNDS PREPARED BY THE METHOD OF EXAMPLE 2

| R$_1$ | R$_2$ | R$_3$ | MS(MH+) |
|---|---|---|---|
| (3-fluoro-6-trifluoromethyl-phenyl)methylamino | Isopropyl | 1-Hydroxymethyl-2-methylpropylamino | 455 |
| [R]-1-(4-methylphenyl)ethylamino | Isopropyl | 2-Aminopropylamino | 368 |
| [R]-1-(2-Naphthyl)ethylamino | Isopropyl | 2-Aminopropylamino | 404 |
| (4-Trifluoromethyl-phenyl)methylamino | Isopropyl | 2-Aminopropylamino | 408 |
| (3-Methylphenyl)methylamino | Isopropyl | 2-Amino-2-methylpropylamino | 368 |
| (2-Chlorophenyl)methylamino | Isopropyl | 2-Amino-2-methylpropylamino | 388 |
| (3-Chlorophenyl)methylamino | Isopropyl | 2-Amino-2-methylpropylamino | 388 |
| (2,5-Difluorophenyl)methylamino | Isopropyl | 2-Amino-2-methylpropylamino | 390 |
| (1-Naphthyl)methylamino | Isopropyl | 2-Amino-2-methylpropylamino | 404 |
| (3,5-Bis-trifluoromethyl-phenyl)methylamino | Isopropyl | 2-Amino-2-methylpropylamino | 490 |
| (2-Trifluoromethyl-phenyl)methylamino | Isopropyl | 2-Amino-2-methylpropylamino | 422 |
| (4-Methylphenyl)methylamino | Isopropyl | 2-Amino-2-methylpropylamino | 368 |
| (4-Chloro-3-trifluoromethyl-phenyl)methylamino | Isopropyl | 2-Amino-2-methylpropylamino | 456 |
| (2-Chloro-5-trifluoromethyl-phenyl)methylamino | Isopropyl | 2-Amino-2-methylpropylamino | 456 |
| (3-Fluoro-6-trifluoromethyl-phenyl)methylamino | Isopropyl | 2-Amino-2-methylpropylamino | 440 |
| [R]-1-(4-Methylphenyl)ethylamino | Isopropyl | 2-Amino-2-methylpropylamino | 382 |
| [R]-1-(2-Naphthyl)ethylamino | Isopropyl | 2-Amino-2-methylpropylamino | 418 |
| (4-Trifluoromethyl-phenyl)methylamino | Isopropyl | 2-Amino-2-methylpropylamino | 422 |

EXAMPLE 3

This Example describes a method for preparing compounds of this invention. The synthesis method disclosed in this Example is only slightly modified from that disclosed in Example 1.

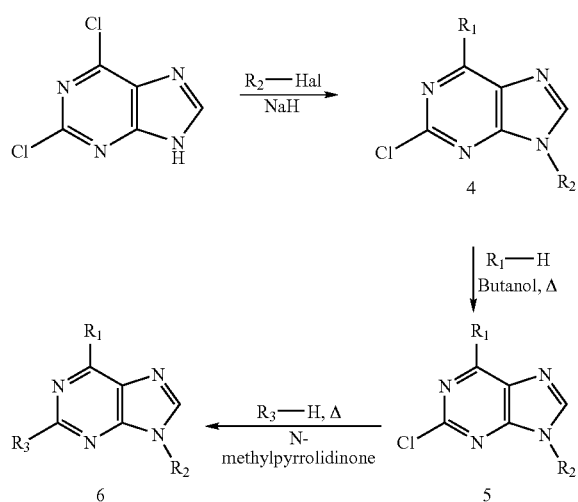

The following compound was prepared according to the method above.

Preparation of 2,6-dichloro-9-isopropylpurine (4)

To a solution of 0.67 g of 2,6-dichloropurine in 5 mL of dry DMF at room temperature was added 0.16 gms (1.1 eq.) of 50% sodium hydride/oil powder. Upon cessation of hydrogen evolution, a large excess (2 mL) of isopropyl iodide was added to the anionic solution. This reaction solution was stirred for three days at ambient temperature. The reaction was quenched with 30 mL of water and extracted with ethyl acetate (350 mL). The organic extracts were combined and back washed with 350 mL of water followed by 20 mL of brine. The ethyl acetate solution was dried over anhydrous magnesium sulfate and evaporated. The compound was subjected to variable gradient flash chromatography on silica gel with hexane/ethyl acetate mixtures and yielded the N-9 product and the N-7 isomer.

Preparation of 2-chloro-6-anilino-9-isopropylpurine (5)

2,6-dichloro-9-isopropylpurine (0.019 g, 0.081 mmol) was dissolved in butanol (0.5 ml) and aniline (0.044 ml, 0.244 mmol) was added. The reaction mixture was heated to 120° C. for 10 hr, cooled, diluted with EtOAc and washed 3 times with water. The mixture was dried over MgSO$_4$ and concentrated to an off white solid.

Preparation of 2-diethanolamino-6-(4-phenylanilino)-9-isopropylpurine (6)

A solution of 67 mgs of 2,6-dichloro-N-9-isopropylpurine and 100 mgs of 4-phenylaniline in 1 mL of n-octanol was heated to 80° C. for 24 hours. The n-octanol was removed in vacuo and then replaced with 1 mL of 40% diethanolamine in DMSO. The solution was heated at 130° C. for 48 hours. The reaction was cooled to ambient temperature then diluted with 10 mL of water and subsequently extracted with ethyl acetate (3×30 mL). The organic extracts were combined and back washed with 3×20 mL of water followed by 10 mL of brine. The ethyl acetate solution was dried over anhydrous magnesium sulfate and filtered and the solvent was evaporated. The 65 mgs of crude product was crystallized from THF-ether solution.

Table 3 below identifies compounds of this invention that were prepared according to the general synthesis method set forth in this Example.

TABLE 3

COMPOUNDS PREPARED BY THE METHOD OF EXAMPLE 3

| $R_1$ | $R_2$ | $R_3$ |
|---|---|---|
| (8-quinolinyl)amino | Isopropyl | Cl |
| (6-quinolinyl)amino | Isopropyl | Cl |
| (3-quinolinyl)amino | Isopropyl | Cl |
| anilino | Isopropyl | Cl |
| 3,5-dinitroanilino | Isopropyl | Cl |
| 4-butylanilino | Isopropyl | Cl |
| (8-quinolinyl)amino | Isopropyl | Diethanolamino |
| (6-quinolinyl)amino | Isopropyl | Diethanolamino |
| (3-quinolinyl)amino | Isopropyl | Diethanolamino |
| anilino | Isopropyl | Diethanolamino |
| 3,5-dinitroanilino | Isopropyl | Diethanolamino |
| 4-butylanilino | Isopropyl | Diethanolamino |
| (6-ethoxy-2-benzothiazolyl)amino | Isopropyl | Cl |
| 4-morpholino-2-methylamino | Isopropyl | Cl |
| (4-aminosulfonyl-phenyl)methylamino | Isopropyl | Cl |
| 4-bromoanilino | Isopropyl | diethanolamino |
| 3,4-dichloroanilino | Isopropyl | diethanolamino |
| 2-(2-(1-methyl)pyrrolidinyl)ethylamino | Isopropyl | diethanolamino |
| 3-bromoanilino | Isopropyl | Cl |
| 4-methoxyanilino | Isopropyl | diethanolamino |
| 4-iodoanilino | Isopropyl | Cl |
| 3-iodoanilino | Isopropyl | Cl |
| 3-methoxyanilino | Isopropyl | Cl |
| 2-(1-piperidinyl)ethylamino | Isopropyl | diethanolamino |
| 2-(1-pyrrolidinyl)ethylamino | Isopropyl | diethanolamino |
| (1-indanyl)amino | Isopropyl | diethanolamino |
| 2-(6-ethoxybenzothiazolyl)amino | Isopropyl | diethanolamino |
| 4-morpholino-2-methylamino | Isopropyl | diethanolamino |
| (4-aminosulfonyl-phenyl)methylamino | Isopropyl | diethanolamino |
| 4-bromoanilino | Isopropyl | diethanolamino |
| 3,4-dichloroanilino | Isopropyl | diethanolamino |
| 2-(2-(1-methyl)pyrrolidinyl)ethylamino | Isopropyl | diethanolamino |
| 3-bromoanilino | Isopropyl | diethanolamino |
| 4-methyoxyanilino | Isopropyl | diethanolamino |
| 4-iodoanilino | Isopropyl | diethanolamino |
| 3-iodoanilino | Isopropyl | diethanolamino |
| 3-methoxyanilino | Isopropyl | diethanolamino |
| 2-(1-piperidinyl)ethylamino | Isopropyl | diethanolamino |
| 2-(1-pyrrolidinyl)ethylamino | Isopropyl | diethanolamino |
| (1-indanyl)amino | Isopropyl | diethanolamino |
| 3-iodonilino | Isopropyl | diethanolamino |
| 3-phenoxyanilino | Isopropyl | diethanolamino |
| 4-iodoanilino | Isopropyl | diethanolamino |
| 4-phenoxyanilino | Isopropyl | diethanolamino |
| 3-phenoxyanilino | Isopropyl | diethanolamino |
| 2-fluorenylamino | Isopropyl | diethanolamino |
| 1-fluorenylamino | Isopropyl | diethanolamino |
| 2-anthracenylamino | Isopropyl | diethanolamino |
| 1-anthracenylamino | Isopropyl | diethanolamino |
| 2-(6-ethoxybenzothiazolyl)amino | Isopropyl | diethanolamino |
| (1-indanyl)amino | Isopropyl | diethanolamino |
| 2-(6-ethoxybenzothiazolyl)amino | Isopropyl | diethanolamino |
| 4-morpholino-2-methylamino | Isopropyl | diethanolamino |
| (4-aminosulfonyl-phenyl)methylamino | Isopropyl | diethanolamino |
| 4-bromoanilino | Isopropyl | diethanolamino |
| 3,4-dichloroanilino | Isopropyl | diethanolamino |
| 2-(2-(1-methyl)pyrrolidinyl)ethylamino | Isopropyl | diethanolamino |
| 3-bromoanilino | Isopropyl | diethanolamino |
| 4-methoxyanilino | Isopropyl | diethanolamino |
| 4-iodoanilino | Isopropyl | diethanolamino |
| 3-iodoanilino | Isopropyl | diethanolamino |
| 3-methoxyanilino | Isopropyl | diethanolamino |
| 2-(1-piperidinyl)ethylamino | Isopropyl | diethanolamino |
| 2-(1-pyrrolidinyl)ethylamino | Isopropyl | diethanolamino |
| (1-indanyl)amino | Isopropyl | diethanolamino |
| 3-iodoanilino | Isopropyl | diethanolamino |
| 3-pheoxyanilino | Isopropyl | diethanolamino |
| 4-iodonilino | Isopropyl | diethanolamino |
| 4-phenoxyanilino | Isopropyl | diethanolamino |
| 3-phenoxyanilino | Isopropyl | diethanolamino |
| 2-fluorenylamino | Isopropyl | diethanolamino |
| 1-fluorenylamino | Isopropyl | diethanolamino |
| 2-anthracenylamino | Isopropyl | diethanolamino |
| 1-anthracenylamino | Isopropyl | diethanolamino |
| 2-(6-ethoxybenzothiazolyl)amino | Isopropyl | diethanolamino |

TABLE 3-continued

COMPOUNDS PREPARED BY THE METHOD OF EXAMPLE 3

| R₁ | R₂ | R₃ |
| --- | --- | --- |
| (2-biphenyl)methylamino | Isopropyl | diethanolamino |
| (4-biphenyl)methylamino | Isopropyl | diethanolamino |
| 2-naphthylmethylamino | Isopropyl | diethanolamino |
| 1-naphthylmethylamino | Isopropyl | diethanolamino |
| (4-Chlorophenyl)methylamino | Isopropyl | Diethanolamino |
| (4-Fluorophenyl)methylamino | Isopropyl | Diethanolamino |
| (4-Methoxyphenyl)methylamino | Isopropyl | 5-Aminopentylamino |
| (4-Trifluoromethylphenyl)methylamino | Isobutyl | Diethanolamino |
| (4-Trifluoromethylphenyl)methylamino | Isopropyl | Diethanolamino |
| (4-Chlorophenyl)methylamino | Isopropyl | (S)-2-Amino-3-phenylpropylamino |
| (4-Fluorophenyl)methylamino | Isopropyl | 2-Aminoethylamino |
| (4-Fluorophenyl)methylamino | Isopropyl | (D)-1-Hydroxymethyl-2-methyl-propylamino |
| (4-Fluorophenyl)methylamino | Isopropyl | (L)-1-Hydroxymethyl-2-methyl-propylamino |
| (4-Chlorophenyl)methylamino | Isopropyl | (D)-1-Hydroxymethyl-2-methyl-propylamino |
| (4-Chlorophenyl)methylamino | Isopropyl | (L)-1-Hydroxymethyl-2-methyl-propylamino |
| (4-Chlorophenyl)methylamino | Isopropyl | 2-Hydroxy-2-phenyl-ethylamino |
| (4-Chlorophenyl)methylamino | Isopropyl | 2-Amino-N1-(2-hydroxyethyl)ethylamino |
| (4-Chlorophenyl)methylamino | Isopropyl | 2-Amino-N2-(2-hydroxyethyl)ethylamino |
| (4-Chlorophenyl)methylamino | Isopropyl | (S)-2-Phenyl-1-carboxamido-ethylamino |
| (4-Chlorophenyl)methylamino | Isopropyl | 2-Amino-N2-(2-hydroxyethyl)-N1-(hydroxyethyl)ethylamino |
| (4-Sulfonamidophenyl)methylamino | Isopropyl | 2-Aminoethylamino |
| (4-Fluorophenyl)methylamino | 2-Oxo-3-butyl | Diethanolamino |
| (4-Fluorophenyl)methylamino | 2-Oxo-3-butyl | 2-Aminoethylamino |
| (4-Chlorophenyl)methylamino | 2-Oxo-3-butyl | Diethanolamino |
| (4-Chlorophenyl)methylamino | 2-Oxo-3-butyl | 2-Aminoethylamino |
| (4-Methylphenyl)methylamino | Isopropyl | 1-Hydroxymethyl-2-methyl-propylamino |
| (3-Methylphenyl)methylamino | Isopropyl | 1-Hydroxymethyl-2-methyl-propylamino |
| (4-Chlorophenyl)methylamino | Isopropyl | 2-(N2-dimethylamino)-N1-benzyl-ethylamino |
| (4-Chlorophenyl)methylamino | Isopropyl | 1-Carboxamido-2-methyl-propylamino |
| (4-Chlorophenyl)methylamino | Isopropyl | 2-Aminoethylamino |
| (4-Chlorophenyl)methylamino | Isopropyl | 3-Aminopropylamino |
| (4-Chlorophenyl)methylamino | Isopropyl | 5-Aminopentylamino |
| (4-Chlorophenyl)methylamino | Isopropyl | 2-Amino-2-methyl-ethylamino |
| (4-Chlorophenyl)methylamino | Isopropyl | (S)-(+)-1-(Hydroxymethyl)propylamino |
| (4-Chlorophenyl)methylamino | Isopropyl | (R)-(−)-1-(Hydroxymethyl)propylamino |
| (4-Chlorophenyl)methylamino | Isopropyl | (S)-(+)-1-(Hydroxymethyl)ethylamino |
| (4-Chlorophenyl)methylamino | Isopropyl | (R)-(−)-1-(Hydroxymethyl)ethylamino |
| (4-Chlorophenyl)methylamino | Isopropyl | (S)-(+)-2-Hydroxypropylamino |
| (4-Chlorophenyl)methylamino | Isopropyl | (R)-(−)-2-Hydroxypropylamino |
| (4-Fluorophenyl)methylamino | Isopropyl | 2-Amino-propylamino |
| (3-Chlorophenyl)methylamino | Isopropyl | Diethanolamino |
| (3-Chlorophenyl)methylamino | Isopropyl | 2-Aminoethylamino |
| (2-Trifluoromethylphenyl methylamino | Isopropyl | Diethanolamino |
| (2-Trifluoromethylphenyl)methylamino | Isopropyl | 2-Aminoethylamino |
| (4-Chloro-3-trifluoromethylphenyl)methylamino | Isopropyl | Diethanolamino |
| (4-Chloro-3-trifluoromethylphenyl)methylamino | Isopropyl | 2-Aminoethylamino |
| (3,5-Dichlorophenyl)methylamino | Isopropyl | Diethanolamino |
| (3,5-Dichlorophenyl)methylamino | Isopropyl | 2-Amino-ethylamino |
| (2-Trifluoromethyl-phenyl)methylamino | Isopropyl | 2-(N2-dimethylamino)-N1-benzyl-ethylamino |
| (3-Chlorophenyl)methylamino | Isopropyl | Diethanolamino |
| (3-Chlorophenyl)methylamino | Isopropyl | 2-Aminoethylamino |
| (2-Trifluoromethylphenyl)methylamino | Isopropyl | Diethanolamino |
| (2-Trifluoromethylphenyl)methylamino | Isopropyl | 2-Aminoethylamino |
| (4-Chloro-3-trifluoromethylphenyl)methylamino | Isopropyl | Diethanolamino |
| (4-Chloro-3-trifluoromethylphenyl)methylamino | Isopropyl | 2-Aminoethylamino |
| (3,5-Dichlorophenyl)methylamino | Isopropyl | Diethanolamino |
| (3,5-Dichlorophenyl)methylamino | Isopropyl | 2-Aminoethylamino |
| (2-Trifluoromethylphenyl)methylamino | Isopropyl | 2-(N2-Dimethylamino)-N1-benzylethylamino |
| (3-Chlorophenyl)methylamino | Isopropyl | 2-(N2-Dimethylamino)-N1-benzylethylamino |
| (3,5-Dichlorophenyl)methylamino | Isopropyl | 2-(N2-Dimethylamino)-N1-benzylethylamino |

TABLE 3-continued

COMPOUNDS PREPARED BY THE METHOD OF EXAMPLE 3

| $R_1$ | $R_2$ | $R_3$ |
|---|---|---|
| (4-Chloro-3-trifluoromethylphenyl)methylamino | Isopropyl | 2-(N2-Dimethylamino)-N1-benzylethylamino |
| (4-Chlorophenyl)methylamino | Isopropyl | 2-Amino-2-methylpropylamino |
| (4-Fluorophenyl)methylamino | Isopropyl | (S)-(2-Tetrahydrofuranyl)methylamino |
| (4-Fluorophenyl)methylamino | Isopropyl | (R)-(2-Tetrahydrofuranyl)methylamino |
| (4-Methylphenyl)methylamino | Isopropyl | Diethanolamino |
| (4-Fluorophenyl)methylamino | Isopropyl | 2-Hydroxy-1-methylethylamino |
| (4-Fluorophenyl)methylamino | Isopropyl | (S)-2-Hydroxy-2-methylethylamino |
| (4-Fluorophenyl)methylamino | Isopropyl | (R)-2-Hydroxy-2-methylethylamino |
| (4-Fluorophenyl)methylamino | Isopropyl | 1-Hydroxymethylpropylamino |
| (4-Flurophenyl)methylamino | Isopropyl | 2-Amino-2-methylpropylamino |

EXAMPLE 4

This Example describes a method for preparing compounds of this invention. The synthesis method disclosed in this Example is only slightly modified from that disclosed in Example 1.

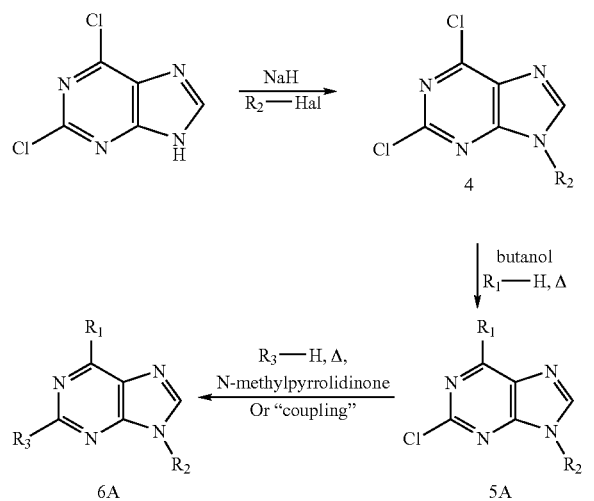

The following compound was prepared according to the method above.

Preparation of 2,6-dichloro-9-isopropylpurine (4)

The 2,6-dichloropurine (5.00 g, 26.46 mmol) was suspended in 55 ml of dry DMF at room temperature and treated with sodium hydride, 60% dispersion (1.27 g, 31.75 mmol) added in portions. After stirring for 1 hr, 2-iodopropane (4.5 ml, 44.98 mmol) was added and the reaction stirred for 2 days. The reaction was poured into diethyl ether and washed once with saturated sodium bicarbonate solution and once with water. The mixture was dried over anhydrous sodium sulfate and concentrated in vacuo. The concentrate was chromatographed over silica gel eluting with 10% acetone in dichloromethane solution to give the desired N-9 alkylation product as a white solid.

Preparation of 2-chloro-6-(4-methylmercapto)anilino-9-isoproplypurine (5A)

2,6-Dichloro-9-isopropylpurine (0.15 g, 0.649 mmol) was dissolved in n-butanol (4 ml) and 4-(methylmercapato)aniline (0.089 ml, 0.714 mmol) and triethylamine (0.20 ml, 1.43 mmol) were added. The reaction mixture was heated at 80° overnight. The cooled reaction was diluted ethyl acetate and washed 1×1M HCI, 1×saturated sodium bicarbonate, and 1×brine before being dried with anhydrous sodium sulfate and concentrated in vacuo. The residue was chromatographed over silica gel and eluting with 2% methanol in dichloromethane to give the desired product as a white solid.

Preparation of 2-diethanolamine-6-(4-methylmercapto)anilino-9-isopropylpurine (6A)

The purine (0.18 g, 539 mmol) was dissolved in N-methylyrrolidinone (3 ml) and diethanolamine (1 ml) and then heated at 120° C. overnight. The cooled reaction was poured into diethyl ether and washed three times with water before drying over anhydrous sodium sulfate and concentrating in vacuo. The residue was chromatographed over silica gel eluting with 5% methanol in dichloromethane to give the desired product as an off-white solid.

$^1$H-NMR($\delta$, CDCl$_3$): 8.08(s,1H), 7.58(d, 2H), 7.47(s,1H), 7.18(d, 2H), 4.95(br s, <2H), 4.52(m, 1H), 3.94(m, 4H), 3.83(m,4H), 2.43(s, 3H), 1.47(d, 6H).

Preparation of 4-(2-thienyl)benzonitrile

Some $R_1$' groups must first be synthesized before reacting with the 2,6-dichloro-9-isopropylpurine. These groups can be synthesized through various coupling methods and other synthetic procedures known to those skilled in the art of organic synthesis.

To a pressure tube was added 4-bromobenzonitrile (0.20 g, 1.10 mmol), tetrakis(triphenylphosphine)palladium (0) (0.127 g, 0.1 eq) and 2-thiopheneboronic acid (0.211 g, 1.65 mmol). The reaction was flushed under vacuum and flushed with dry nitrogen three times. Following flushes, ethyleneglycol dimethyl ether (5.5 ml) and an aqueous solution of sodium carbonate (2.53 ml, 1M) were added to the tube. The tube was then sealed and heated at 80° C. overnight. The cooled reaction was the diluted with diethyl ether and washed twice with water before drying over sodium sulfate and concentrating in vacuo. The residue was chromatographed over silica gel eluting with 10% ethyl acetate in hexane to give the desired product as a white solid.

Preparation of 4-(2-thienyl)benzylamine

The 4-(2-thienyl)benzonitrile (0.086 g, 0.464 mmol) was dissolved in dry tetrahydrofuran (1.6 ml) before lithium aluminum hydride (0.46 ml, 0.464 mmol, 1 M in THF) was added dropwise. The reaction was allowed to stir at room temperature overnight. TLC (5% methanol in dichloromethane) still showed starting material remaining. Another 1 eq of LAH was added. After an additional hour, the reaction was quenched by the Fieser and Fieser method using wager (17.46 µl), aqueous sodium hydroxide solution (1 7.46 µl, 15% soln.), and water (52.37 µl) added sequentially to the reaction. The reaction was then diluted with diethyl ether and water and extracted twice with diethyl ether before drying over sodium sulfate and concentrating in vacuo. The residue was carried on crude without any further purification.

Table 4 below identified compounds of this invention that were prepared according to the general synthesis method set forth in this Example.

TABLE 4

COMPOUNDS PREPARED BY THE METHOD OF EXAMPLE 4

| $R_1'$-X | $R_2$ | $R_3$ |
|---|---|---|
| Cl | Me | Cl |
| Ethanolamino | Me | Ethanolamino |
| Cyclopropylmethylamino | Isopropyl | Cl |
| Cyclopropylmethylamino | Isopropyl | Diethanolamino |
| 3,5-dinitroanilino | Isopropyl | Cl |
| 3-phenoxyanilino | Isopropyl | Cl |
| 4-iodoanilino | Isopropyl | Cl |
| 3-aminoquinolino | Isopropyl | Cl |
| 3,5-dinitroanilino | Isopropyl | Diethanolamino |
| Cl | Epoxymethyl | Cl |
| 4-methoxybenzylamino | 2,3-dihydroxypropyl | Diethanolamino |
| 4-phenylanilino | Isopropyl | Diethanolamino |
| 4-phenylbenzylamino | Isopropyl | Cl |
| 2-naphthalenylmethylamino | Isopropyl | Cl |
| 1-naphthalenylmethylamino | Isopropyl | Cl |
| 2-phenylbenzylamino | Isopropyl | Cl |
| 3-quinolinylamino | Isopropyl | Diethanolamino |
| 5-quinolinylamino | Isopropyl | Diethanolamino |
| 6-quinolinylamino | Isopropyl | Diethanolamino |
| 8-quinolinylamino | Isopropyl | Diethanolamino |
| N-butylamino | Isopropyl | Cl |
| 4-(2-thiophenyl)benzylamino | Isopropyl | Deithanolamino |
| 4-(2-thiophenyl)benzylamino | Isopropyl | Cl |
| 3-thiomethoxyanilino | Isopropyl | Cl |
| 4-thiomethoxyanilino | Isopropyl | Cl |
| 3-thiomethorxyanilino | Isopropyl | Diethanoamino |
| 4-thiomethoxyanilino | Isopropyl | Diethanoamino |
| 4-(2-pyridinyl)benzylamino | Isopropyl | Cl |
| 3-methoxybenzylamino | Isopropyl | Cl |
| 3,4-dimethoxybenzylamino | Isopropyl | Cl |
| 3,4,5-trimethoxyenzylamino | Isopropyl | Cl |
| 3-methoxybenzylamino | Isopropyl | Diethanolamino |
| 3,4-dimethoxybenzylamino | Isopropyl | Diethanolamino |
| 3,4,5-trimethoxbenzylamino | Isopropyl | Diethanolamino |
| 4-(3-thiophenyl)benzylamino | Isopropyl | Cl |
| 4-(4-methoxphenyl)benzylamino | Isopropyl | Cl |
| 4-(4-bromophenyl)benzylamino | Isopropyl | Diethanolamino |
| 4-(3-methoxyphenyl)benzylamino | Isopropyl | Diethanolamino |
| 4-(4-methoxypheny)benzylamino | Isopropyl | Diethanolamino |
| 4-(3-thiophenyl)benzylamino | Isopropyl | Diethanolamino |
| 4-(3-methylpheny)benzylamino | Isopropyl | Cl |
| 4-(4-methylphenyl)benzylamino | Isopropyl | Cl |
| 4-(4-trifluoromethylphenyl)benzylamino | Isopropyl | Cl |
| 3-(4 nitrilophenyl)anilino | Isopropyl | Cl |
| 3-(4-nitrilophenyl)anilino | Isopropyl | Diethanolamino |
| 4-(2-pyridinyl)benzylamino | Isopropyl | Cl |
| 4-(2-pryidinyl)benzylamino | Isopropyl | Diethanolamino |

EXAMPLE 5

This Example describes a method for preparing compounds of this invention. The synthesis method disclosed in this Example is only slightly modified from that disclosed in Example 1.

Preparation of 2-amino-6-chloro-9-methylpurine

The 2-amino-6-chloropurine (1.08 g, 6.4 mmol) was suspended in dry DMF (75 ml) and treated with sodium hydride, 60% dispersion (0.28 g, 7 mmol). The suspension was stirred for 15 min before iodomethane (0.44 ml, 7.06 mmol) was added and the resulting yellow solution stirred for 1 hr 45 min. The solid was filtered and the filtrate evaporated before addition of water for 10 min. The resulting solid was filtered and dried overnight to give the product as a mixture of N-7 and N-9 alkylation products. The residual liquor was left overnight and more crystals were collected the next day and dried.

Preparation of 6-chloro-2-(2-methoxyacetylamino)-9-methylpurine

The mixture of isomers from above was dissolved in dichloromethane and pyridine (2 eq) followed by treatment with methoxyacetyl chloride (4 eq). The reaction was stirred at room temperature until complete. The reaction was evaporated and filtered through a plug of silicia gel eluting with 2% methanol in dichloromethane followed by purification on a chomatotron using silica gel and eluting with 2% methanol in dichloromethane to isolate the desired product.

Table 5 identifies compounds of this invention that were prepared according to the synthesis method set forth in this Example.

TABLE 5

COMPOUNDS PREPARED BY THE METHOD OF EXAMPLE 5

| $R_1$ | $R_2$ | $R_3$ |
|---|---|---|
| Cl | Me | H |
| Cl | Me | 2-methoxyacetylamino |

EXAMPLE 6

This Example describes a method for preparing compounds of this invention. The synthesis method disclosed in this Example is only slightly modified from that disclosed in Example 1.

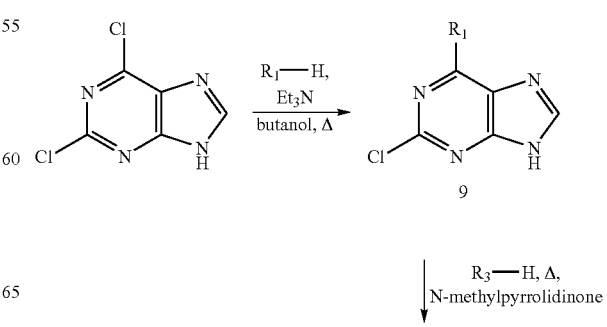

-continued

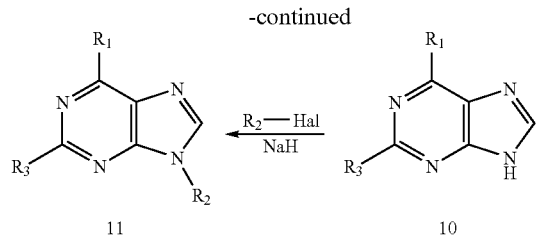

The following compound was prepared according to the method above.

Preparation of 2-chloro-6-(4-phenyl benzylamino)purine (9)

The 2,6-dichloropurine (5.0 g, 26.45 mmol) was suspended in n-butanol (50 ml) and the 4-phenylbenzylamine (6.61 g, 29.1 mmol) and triethylamine (4.1 ml, 29.1 mmol) were added. The solution was heated at 120° C. overnight then cooled. Filtered off product using excess n-butanol and washed precipitate with 100 ml 1M HCl and 200 ml water. The solid was dried in vacuum over overnight at 70° C. to give the desired product as a pale yellow solid Preparation of 2-diethanolamino-6-(4-phenyl benzylamino)purine (10)

The 2-chloro-6-(4-phenyl benzylamino)purine (2.0 g, 5.96 mmol) was added together with diethanolamine (11.4 ml, 119.2 mmol) and N-methylpyrrolidinone (10 ml) and heated at 120° C. overnight. The cooled reaction was poured into dichloromethane and washed twice with water. The organic layer was dried with anhydrous sodium sulfate and concentrated in vacuo to give the desired product as a pale green solid that was further dried in vacuum oven at 70° C. for 2 days.

Preparation of 2-diethanolamino-6-(4-phenyl benzylamino)-9-methylpurine (11)

The 2-diethanolamino-6-(4-phenyl benzylamino)purine (0.050 g, 0.124 mmol) was dissolved in dry DMF and treated wit sodium hydride, 60% dispersion (5.5 mgs, 0.136 mmol) for 1 hr. iodomethane (0.009 ml, 0.148 mmol) was added and the resultant solution stirred at room temperature overnight. Poured reaction into diethyl ether and washed twice with saturated sodium bicarbonate solution before drying over anhydrous sodium sulfate and concentrating in vacuo. The residue was chromatographed over silica gel eluting with 5% methanol in dichloromethane to give the produce as a white solid.
$_1$H-NMR($\delta$, CDCl3): 7.55 (m,4H), 7.41 (m, 4H) 7.35(m, 4H), 6.41 (br s, <1H), 5.10(br s, <2H), 4.72 (br s, 2H), 3.86 (m, 4H), 3.74(m, 4H), 3.59(s, 3H).

Table 6 identified compounds of this invention that were prepared according to the synthesis method set forth in this Example.

TABLE 6

| COMPOUNDS PREPARED BY THE METHOD OF EXAMPLE 6 | | |
|---|---|---|
| $R_1$'-X | $R_2$ | $R_3$ |
| 4-phenylbenzylamino | Methyl | diethanolamino |
| 4-phenylbenzylamino | Cyclopentyl | diethanolamino |

TABLE 6-continued

| COMPOUNDS PREPARED BY THE METHOD OF EXAMPLE 6 | | |
|---|---|---|
| $R_1$'-X | $R_2$ | $R_3$ |
| 4-phenylbenzylamino | Allyl | diethanolamino |
| 4-phenylbenzylamino | Benzyl | diethanolamino |
| 4-phenylbenzylamino | 3-methylbutyl | diethanolamino |
| 4-phenylbenzylamino | Isobutyl | diethanolamino |
| 4-phenylbenzylamino | t-butylacetate | diethanolamino |
| 4-phenylbenzylamino | Methylacetate | diethanolamino |
| 4-phenylbenzylamino | Cyclobutyl | diethanolamino |
| 4-phenylbenzylamino | Ethyl | diethanolamino |
| 4-phenylbenzylamino | Propyl | diethanolamino |

EXAMPLE 7

Compositions of this invention were evaluated in the following assays.

CDK$_2$ Assays

Compositions of this invention were assayed to determine their CDK$_2$ inhibitory activity. The assay system (total volume of 50 μl) contained 50 mM Tris-Cl, pH 7.4, 10 mM MgCl$_2$, 5 mM DTT, 1 μg of histone H1, 30 μM ATP (1 μCi of gamma$^{32}$P labeled ATP), 10 μg of BSA and 1 ng of purified CDK$_2$. After incubation at 30° C. for 30 min, the reaction was terminated by the addition of 10 μl of 10% TCA and the samples were blotted onto to nitrocellulose filters. These filters were washed extensively in 10% TCA and assayed for radioactivity. Blanks contained no enzyme. To ascertain the potency of various compounds of this invention, the compounds were added to the above assay at concentrations ranging from 100 to 0.02 μg/ml. After incubation at 30 min., the assay tubes were processed as above. In all assays, various concentrations of olomoucine were added and were used as a standard positive control. The IC$_{50}$ (enzyme) listed in Table 7 is defined as the concentration required to inhibit CDK2 activity by 50%.

EXAMPLE 8

Cell Proliferation Assays

Early passage rat aortic smooth muscle cells (CV Therapeutics Cell repository) were seeded in 48 well dishes (Falcon, ml/well) at a density of 20,000 cells/ml of DME containing 5% heat inactivated bovine serum. The cells were incubated in a standard tissue culture incubator for 48 hr. The medium was aspirated and the wells were replenished with 0.2 ml of fresh medium. Compounds of this invention were added at concentrations ranging from 100 to 0.37 μg/ml. After 48 hr incubation, the medium was aspirated and the cultures were treated with 0.2 ml of saline 0.25 μl of phenozine methosulfate solution containing MTS (Cell Titer 96® Aqueous Non-radioactive cell proliferation assay kit, Catalog #G 5430, Promega, 2800 Woods Hollow Road, Madison, Wis. 53711-5399). The IC$_{50}$ cells listed in Table 7 is defined as the concentration required to inhibit cell proliferation by 50%. Olomoucine at various concentrations was added and was used as a standard positive control.

TABLE 7

BIOACTIVITY OF SELECTED REPRESENTATIVES OF THIS INVENTION

| $R_1$ | $R_2$ | $R_3$ | $IC_{50}$ (µg/mL) enzyme | $IC_{50}$ (µg/mL) cells |
|---|---|---|---|---|
| benzylamino | Me | Ethanolamino | 7 | 70 |
| 4-methoxybenzylamino | H | Cl | 60 | NA |
| 4-methoxybenzylamino | Me | Cl | 6 | >70 |
| 4-methoxybenzylamino | Me | Ethanolamino | 4 | 48 |
| 4-chlorobenzyloxy | H | Cl | 60 | NA |
| 4-chlorobenzyloxy | Me | Cl | 60 | NA |
| 4-chlorobenzyloxy | trifluoromethyl | Cl | >60 | NA |
| 4-methoxybenzylamino | isopropyl | Cl | 4 | 77 |
| 4-methoxybenzylamino | isopropyl | Ethanolamino | 4 | 43 |
| 4-methoxybenzylamino | Me | Diethanolamino | 4 | 48 |
| 4-methoxybenzylamino | 2-methylpropyl | Cl | 60 | >70 |
| ethanolamino | Me | Ethanolamino | >60 | >70 |
| 4-methoxybenzylamino | trifluoromethyl | Cl | >60 | >70 |
| 4-methoxybenzylamino | benzyl | Cl | >60 | >70 |
| ethanolamino | H | Benzylamino | >60 | NA |
| 4-methoxybenzylamino | isopropyl | Diethanolamino | 0.2 | 2.1 |
| 4-methoxybenzylamino | perfluoroisopropyl | Cl | >45 | NA |
| 4-methoxybenzylamino | perfluoroisopropyl | Diethanolamino | 40 | NA |
| 4-methoxybenzylamino | ispropyl | 3-pyrroline | 1 | 12.5 |
| 4-methoxybenzylamino | hydroxyethyl | Diethanolamino | 0.5 | 62 |
| 4-methoxybenzylamino | isopropyl | 2-hydroxy-1-1-hydroxymethylethylamino | 0.4 | 15 |
| 4-methoxybenzylamino | isopropyl | 3-amino-2-hydroxypropyl amino | 0.6 | 25 |
| 4-methoxybenzylamino | 3-cyanopropyl | Cl | >60 | NA |
| 4-methoxybenzylamino | 3-chloropropyl | Cl | >60 | NA |
| 4-methoxybenzylamino | benzyl | Cl | >60 | NA |
| 4-methoxybenzylamino | Methyl 4-carboxybenzyl | Cl | 60 | NA |
| 4-methoxybenzylamino | Naphthaloylethyl | | >60 | NA |
| 4-chlorobenzylamino | Trifluoromethyl | Cl | 1 | NA |
| 4-methoxybenzylamino | isopropyl | N-(2-cyanopropyl)-N-(3-pyridylmethyl)-amino | 1 | NA |
| 4-methoxybenzylamino | isopropyl | 2-(hydroxymethyl)-3-methylbutan-2-amino | 1 | NA |
| 4-methoxybenzylamino | isopropyl | 3-hydroxypiperidino | 1 | NA |
| cyclohexylmethylamino | isopropyl | Cl | 1 | NA |
| piperonylamino | isopropyl | Diethanolamino | 0.8 | NA |
| 4-methoxybenzylamino | isopropyl | Diisopropanolamino | 0.8 | NA |
| anilino | isopropyl | Cl | 1 | NA |
| 4-methoxybenzylamino | isopropyl | N-benzyl-N-2-hydroxyethylamino | 1 | NA |
| 4-phenylanilino | isopropyl | Diethanolamino | 0.6 | NA |
| 4-phenylbenzylamino | isopropyl | Diethanolamino | 0.6 | NA |
| 4-phenylbenzylamino | isopropyl | 3-amino-1,2-propanediol | 0.6 | NA |
| 4-(2-thiophenyl)benzylamino | isopropyl | Diethannolamino | 0.5 | NA |
| 4-(4-methylphenyl)benzylamino | isopropyl | Diethanolamino | 0.6 | NA |
| 4-(4-trifluoromethylphenyl)benzyalmino | isopropyl | Diethanolamino | 0.6 | NA |
| 4-thiomethoxyanilino | isopropyl | Cl | 0.6 | NA |
| 3-(4-nitrilophenyl)anilino | isopropyl | Diethanolamino | 0.5 | NA |
| 3-thiomethoxyanilino | isopropyl | Diethanolamino | 0.1 | NA |
| 4-thiomethoxyanilino | isopropyl | Diethanolamino | 0.07 | NA |
| 3-methoxybenzylamino | isopropyl | Cl | 0.9 | NA |
| 4-(2-pyridinyl)benzylamino | isopropyl | Diethanolamino | 0.16 | NA |
| 3-methoxybenzylamino | Isopropyl | Diethanolamino | 0.5 | NA |
| (4-Chlorophenyl)methylamino | Isopropyl | Diethanolamino | 0.12 | 0.3 |
| (4-Fluorophenyl)methylamino | Isopropyl | Diethanolamino | 0.15 | 2.2 |
| (4-Trifluoromethylphenyl)methylamino | Isobutyl | Diethanolamino | 59 | NA |
| (4-Trifluoromethylphenyl)methylamino | Isopropyl | Diethanolamino | 0.56 | NA |
| (4-Chlorophenyl)methylamino | Isopropyl | (S)-2-Amino-3-phenylpropylamino | 1.07 | NA |
| (4-Fluorophenyl)methylamino | Isopropyl | 2-Aminoethylamino | 0.17 | 1.4 |
| (4-Fluorophenyl)methylamino | Isopropyl | (D)-1-Hydroxymethyl-2-methyl-propylamino | 0.06 | 2.7 |
| (4-Fluorophenyl)methylamino | Isopropyl | (L)-1-Hydroxymethyl-2-methyl-propylamino | 0.19 | NA |
| (4-Chlorophenyl)methylamino | Isopropyl | (D)-1-Hydroxymethyl-2-methyl-propylamino | 0.19 | NA |
| (4-Chlorophenyl)methylamino | Isopropyl | (L)-1-Hydroxymethyl-2-methyl-propylamino | 0.05 | NA |
| (4-Chlorophenyl)methylamino | Isopropyl | 2-Hydroxy-2-phenyl-ethylamino | 0.08 | >5 |
| (4-Chlorophenyl)methylamino | Isopropyl | 2-Amino-N1-(2-hydroxyethyl)ethylamino | 0.07 | 0.2 |

TABLE 7-continued

BIOACTIVITY OF SELECTED REPRESENTATIVES OF THIS INVENTION

| R₁ | R₂ | R₃ | IC₅₀ (μg/mL) enzyme | IC₅₀ (μg/mL) cells |
|---|---|---|---|---|
| (4-Chlorophenyl)methylamino | Isopropyl | 2-Amino-N2-(2-hydroxyethyl)ethylamino | 2.02 | NA |
| (4-Chlorophenyl)methylamino | Isopropyl | (S)-2-Phenyl-1-carboxamido-ethylamino | 1.07 | NA |
| (4-Chlorophenyl)methylamino | Isopropyl | 2-Amino-N2-(2-hydroxyethyl)-N1-(hydroxyethyl)ethylamino | 0.43 | NA |
| (4-Sulfonamidophenyl)methylamino | Isopropyl | 2-Aminoethylamino | 9 | NA |
| (4-Fluorophenyl)methylamino | 2-Oxo-3-butyl | Diethanolamino | 11 | NA |
| (4-Chlorophenyl)methylamino | 2-Oxo-3-butyl | Diethanolamino | 37 | NA |
| (4-Chlorophenyl)methylamino | Isopropyl | 2-Aminoethylamino | 0.35 | 0.1 |
| (4-Chlorophenyl)methylamino | Isopropyl | 3-Aminopropylamino | 1.0 | NA |
| (4-Chlorophenyl)methylamino | Isopropyl | 5-Aminopentylamino | 31 | NA |
| (4-Chlorophenyl)methylamino | Isopropyl | 2-Amino-2-methyl-ethylamino | 0.05 | 0.1 |
| (4-Chlorophenyl)methylamino | Isopropyl | (S)-(+)-1-(Hydroxymethyl)propylamino | 0.17 | NA |
| (4-Chlorophenyl)methylamino | Isopropyl | (R)-(−)-1-(Hydroxymethyl)propylamino | 0.18 | NA |
| (4-Chlorophenyl)methylamino | Isopropyl | (S)-(+)-1-(Hydroxymethyl)ethylamino | 0.26 | NA |
| (4-Chlorophenyl)methylamino | Isopropyl | (R)-(−)-1-(Hydroxymethyl)ethylamino | 0.35 | NA |
| (4-Chlorophenyl)methylamino | Isopropyl | (S)-(+)-2-Hydroxypropylamino | 0.38 | NA |
| (4-Chlorophenyl)methylamino | Isopropyl | (R)-(−)-2-Hydroxypropylamino | 0.43 | NA |
| (4-Fluorophenyl)methylamino | Isopropyl | 2-Amino-propylamino | 0.48 | NA |
| (4-Fluorophenyl)methylamino | Isopropyl | (S)-(2-Tetrahydrofuranyl)methylamino | 0.63 | NA |
| (4-Fluorophenyl)methylamino | Isopropyl | (R)-(2-Tetrahydrofuranyl)methylamino | 0.58 | NA |
| (4-Fluorophenyl)methylamino | Isopropyl | 2-Hydroxy-1-methylethylamino | 0.18 | NA |
| (4-Fluorophenyl)methylamino | Isopropyl | (S)-2-Hydroxy-2-methylethylamino | 0.22 | NA |
| (4-Fluorophenyl)methylamino | Isopropyl | (R)-2-Hydroxy-2-methylethylamino | 0.23 | >5 |
| (4-Fluorophenyl)methylamino | Isopropyl | 1-Hydroxymethyl propylamino | 0.11 | 2.4 |

The inhibition of cell proliferation properties of the compounds of this invention are demonstrated by their ability to inhibit cell proliferation in the range of about 0.05 μg/ml to 100 μg/ml, preferably less than 0.5 μg/ml.

Similar assays were performed using the following cell lines; P388—mouse lymphoid neoplasm; L1210—mouse lymphcytic leukemia; Caco2 human colon adenocarcinoma; MCF7 human breast adenocarcinoma; PupVSMC rat neonatal aortic smooth muscle cells; Ovcar human ovarian Carcinoma; Panc1 human pancreatic adenocarcinoma; and HUVEC human umbilical cord endothelial cells. The inhibitory activity of several compositions of this invention against one or more of the cell lines are reported in Tables 8 and 9 below.

TABLE 8

IC₅₀ (μG/ML) FOR INHIBITION OF CELL PROLIFERATION

| R₁X | R₂ | R₃ | P 388 | L 120 | Caco2 | MCF7 | Panc1 | OvCar | Pup VSMC | HUVEC |
|---|---|---|---|---|---|---|---|---|---|---|
| (4-methoxyphenyl)-methylamino | Isopropyl | Diethanol-amino | 1.5 | 2.5 | 4.5 | 8.0 | 10.0 | 11.0 | 0.5 | 3.0 |
| (4-phenylphenyl)amino | Isopropyl | Diethanol-amino | 1.0 | 4.0 | 0.5 | 4.0 | 4.0 | 7.0 | 1.0 | |
| (4-phenylphenyl)-methylamino | Isopropyl | Diethanol-amino | <1.0 | 1.0 | 3.5 | 1.0 | 1.3 | 2.0 | | |
| (4-methoxyphenyl)-methylamino | Isopropyl | Morpholino | >5 | | | | 5.5 | 4.0 | | |
| 3-phenoxyphenyl,3-benzyloxyphenyl | isopropyl | Diethanol-amino | 1.5 | | | 2.0 | 2.5 | 2.0 | | |

TABLE 9

| R₁X | R₂ | R₃ | MRC-5 | PupVSMC |
|---|---|---|---|---|
| (4-methoxyphenyl)methylamino | Isopropyl | Diethanolamino | 5 | 0.4 |
| (4-Chlorophenyl)methylamino | Isopropyl | 2-Aminoethylamino | 1 | 0.1 |
| (4-Chlorophenyl)-methylamino | Isopropyl | 2-Amino-2-methylethylamino | 1 | 0.1 |

TABLE 9-continued

| R₁X | R₂ | R₃ | MRC-5 | PupVSMC |
|---|---|---|---|---|
| (4-Chlorophenyl)-methylamino | Isopropyl | 2-Amino-N1-(2-hydroxyethyl)ethylamino | 1 | 0.3 |
| (4-Chlorophenyl)-methylamino | Isopropyl | Diethanolamino | 3 | 0.3 |

MRC-5 = Human Fibroblast
PupVSMC = Rat neonatal aortic smooth muscle cells

EXAMPLE 8

Compounds of this invention were evaluated for effectiveness using the Murine Leukemia Model. The Murine Leukemia Model is a standard model used in the evaluation of antitumor agents. CDF1 mice were injected ip with L1210 cells ($1\times10^3$ cells/mouse). Twenty-four hours later, these mice were treated with various doses (ip) of compound 3 of Example 1 in saline. The dosing regimen used in this study is outlined in Table 10, below. Mice were dosed with compound 3 daily or on alternate days. Control mice received saline. After 7 days, dosing was suspended and survival monitored.

TABLE 10

| Treatment | | N | Median survival time Days | T/C × 100 |
|---|---|---|---|---|
| Saline control | | 7 | 10 (9–13) | 100 |
| Compound 3 | 0.5 mg/kg bid | 7 | 11 (10–15) | 110 |
| | 1.0 mg/kg bid | 7 | 13 (11–13) | 130 |
| | 2 mg/kg bid | 7 | 12 (10–14) | 120 |
| | 4 mg/kg - days 1, 3, 5, 7 | 7 | 13 (10–15) | 130 |
| | 8 mg/kg - days 1, 3, 5, 7 | 7 | 13 (12–16) | 130 |

The results indicate that rats administered compound 3 survived longer than the control rats.

EXAMPLE 9

This example measured the effect of an acute local delivery of compound 3 of Example 1 in reducing neointima formation following balloon angioplasty in the rat carotid artery model. In this example, the left common carotid arteries of adult male rats (n=10 per experimental group) were surgically injured using a Fogarty arterial embolectomy catheter. Immediately after injury, the common carotid artery was bisected with a vascular clamp, thereby establishing an untreated and treated segment. A drug delivery catheter was then inserted into the distal half of the common carotid. After drug delivery, the catheter was removed and excess drug was washed out by removing the vascular clamp and re-establishing blood flow before closing the artery. The animals were allowed to recover for 14 days before harvesting the common carotid artery. The harvested tissue was sectioned and the neointimal area was digitized and measured with a computer planimetery system. For each animal, 15 measurements were averaged for the untreated segment and 15 for the treated. {2-[(2-aminoethyl)amino]-9-(methylethyl)purin-6-yl}[(4-chlorophenyl)methyl]amine was administered at a dose of 5 mg/mL reducing the neointimal area about 90% in comparison to the 6% reduction of saline alone.

The results of this Example are found in FIG. 1. According to FIG. 1, administering compound 3 of Example 1 to a damaged carotid artery reduced the neointimal area about 88% in comparison to the 6% reduction produced by the saline vehicle alone.

EXAMPLE 10

IκB-α Kinase Assays

Compositions of this invention were assayed to determine their IκB-α kinase inhibitory activity. The human umbilical vein endothelial cell line (HUVEC) used in these studies was purchased from Clonetics (San Diego, Calif.) and was maintained in endothelial cell growth medium supplemented with 2% fetal bovine serum, 10 ng/ml human recombinant epidermal growth factor, 1 µg/ml hydrocortisone, 50 µg/ml gentamicin, 50 ng/ml amphotericin B and 12 µg/ml bovine brain extract at 37° C. in a tissue culture incubator. All growth media and supplements were purchased from Clonetics (San Diego, Calif.). *E. coli* lipopolysaccharide (LPS) serotype 0111:B4 was purchased from Sigma (Saint Louis, Mich.). All other chemicals were of reagent grade.

Preparation of cell Lysate

Monolayers (75 cm²) of HUVEC cells were treated with LPS (100 ng/ml) for 5 minutes after which the cell media was rapidly removed and the monolayer washed three times with ice cold PBS. The cell layer was scraped into 10 ml PBS and the cells pelleted by centrifugation (3000 rpm, 5 min, 4° C.). Cell lysate was prepared by incubating the cell pellet in 0.2 ml lysis buffer (20 mM HEPES, pH7.3, 50 mM NaCl, 10 mM MgCl₂, 1 mM EDTA, 1 mM EGTA, 1 mM sodium orthovanadate, 10 mM β-glycerophospate, 1 mM phenylmethylsulfonylfuoride, 1 mM dithiothreitol, 0.5% Nonidet P-40 for 15 minutes at 37° C. for frequent vortexing. Cell debris was removed from the sample by microcentrifugation (10,000×g, 15 minutes, 4° C.) and the supernatant was "precleared" by the addition of 100 ml of a suspension of sepharose 4B in lysis buffer and mixing gently for 1 hour at 4° C. The sepharose 4B beads were removed by microcentrifugation and the supernatant aliquotted and stored at 80° C.

Solid Phase IκB-α Kinase Assay

1 µg of GST-IκB-α, corresponding to full length IκB-α of human origin, (Santa Cruz Biotechnology,) was incubated with 20 µl of a 50% slurry of glutathione S sepharose 4B (Pharmacia) in reaction buffer (20 mM HEPES, pH7.3, 10 mM MgCl₂, 15 mM β-glycerophosphate, 0.5 mM sodium orthovanadate, 0.5 mM EGTA) for 30 minutes at room temperature. The GST- IκB-bead complex was the washed three times with 0.5 ml of reaction buffer by resuspension and microcentrifugation. 10 µg of HUVEC cell lysate protein in 100 µl of reaction buffer was then added to the GST-IκB-bead complex and the mixture incubated with gentle mixing at 4° C. for 1 hour. The bead complex was then washed three times with reaction buffer containing 0.2 M NaCl and once with reaction buffer alone. Finally the bead complex was resuspended in 20 µl of reaction buffer containing 5 µCi [y-$^{32}$P]ATP (>5000 ci/mmol, New England Nuclear Corp. Boston, Mass.) and incubated at room temperature for 15 minutes. The reaction was terminated by the addition of 10 µl of SDS-PAGE sample buffer and boiled for 3 minutes before separation by SDS-PAGE (10–20% gradient Readygel, BioRad). Following electrophoresis the gel was fixed (50% methanol 10% acetic acid) for 15 minutes, washed three times for 5 minutes each with distilled H$_2$O and treated with 5% glycerol for 15 minutes before drying down and exposing to film for autoradiography (X-OMAT XAR-5 Kodak).

In Gel Kinase Assay

IκB-α isozymes were assayed for activity using a modification of previously published methods (11, 19, 20). Briefly duplicate samples of the IκB-glutathione sepharose 4B bead complex were prepared as described above and were separated by electrophoresis through a 12% SDS-PAGE gel which had been polymerized in the presence of 15 µg/ml GST-IκB-α. Following electrophoresis the gel was washed gently twice for 30 minutes each with 50 mM Tris-HCl pH8.0, 5 mM β-mercaptoethanol; 20% isopropanol to remove SDS. Proteins were then denatured within the gel by incubation for 45 minutes in 100 ml 50 mM Tris-HCl pH8.0; 5 mM β-mercaptoethanol; 0.04% Tween 40. The gel was then cut in half to separate the duplicate samples, one half was incubated in 10 ml reaction buffer alone and the other in 10 ml reaction buffer containing 10 µg/ml of 2-diethanolamino-6(4-phenyl anilino)-9-isopropyl purine (compound 6 of Example 2) for 1 hour at room temperature which 10 µCi[y-$^{32}$ P]ATP was added and the incubations continued for a further hour at room temperature. The gels were then subjected to multiple 15-minute washes of 100 ml each 5% trichloroacetic acid containing 1% sodium pyrophosphate until 1 ml of wash solution gave close to background radioactivity. The gels were then dried down and exposed to file for autoradiograhy.

Preparation of 2-diethanolamino-6-(4-phenybenzylamino)-9-isopropyl purine Epoxy Activated Sepharose 6B Affinity Matrix Freeze dried epoxy activated Sepharose 6B (Pharmacia LKB, Piscataway, N.J.) was chosen for the coupling reaction due to its ability to form an ether bond between an hydroxyl-containing ligand and the epoxide group on the sepharose. The gel was swollen according to the manufacturer's instructions, (100 mg) of compound 6 of Example 2 was dissolved in 1 ml coupling solution (1.2:1 v/v dimethylformamide : 0.1N NaOH) and mixed with 0.5 ml of swollen gel at pH 10–11 for 72 hours at room temperature with gentle agitation. Excess reactive groups were blocked with 1M ethanolamine for 4 hours at 50° C. and the gel slurry was poured into 1 ml syringe column. The resin was activated with three alternating cycles of twenty column volumes each of pH 4.0 (0.1M acetate, 0.5M NaCl) and pH 8.0 (0.1M Tris-HCl, 0.5M NaCl) buffers followed by twenty column volumes of reaction buffer (20 mM HEPES, pH7.3, 10 mM MgCl$_2$, 15 mM β-glycerophophate, 0.5 mM sodium orthovanadate, 0.5 mM EGTA). The column was stored at 4° C. in reaction buffer containing 0.5% sodium azide and regenerated prior to each use with alternating cycles of low and high pH as described above.

Activated HUVEC cell lysate (500 µg protein in 1 ml reaction buffer) was passed over the CVT-1545 sepharose matrix sequentially five times and the flow through was saved (unbound material). The matrix was then washed three times with 1 ml of reaction buffer (wash 1–3) then three times each with reaction buffer containing 0.5M NaCl (eluate 1–3). Aliquots (20 µl from 1 ml) of each sample were assayed for their ability to phosphorylate at GST- IκB-sepharose bead complex and analyzed by SDS-PAGE as described above.

Assay of Affinity Enriched IκB-α Kinase

The bulked 0.5 M NaCl eluates from the affinity matrix were used as the source of enzyme for development of an IκB-α kinase filter assay. Each reaction contained affinity enriched IκB-α kinase (1 µg protein), 10 ng GST IκB-α kinase and 0.5 µCi[y-$^{32}$P]ATP (>5000 Ci/mmol, New England Nuclear Corp, Boston, Mass.) in 20 µl reaction buffer. The reaction was incubated for 15 minutes at room temperature and was terminated by the addition of 2 µl 0.5M EDTA. Reaction mixtures were blotted onto phosphocellulose disks (Gibco BRL Life Technologies, Gaithersburg, Md.) and the filters washed three times with 0.15M phosphoric acid with gentle shaking for 15 minutes (up to ten filters were washed with 300 ml of 0.15M phosphoric acid.) Following a third wash the filters were air dried, added to scintillation fluid and assayed by liquid scintillation spectrometry.

Electrophoretic Mobility Shift Assay

Nuclear extracts were prepared using a high-salt buffer extraction procedure. 10 pmol of double stranded NF-κB consenses oligonucleotide (5'-AGTTGAGGGGACTTTC-CCAGGC-3') )Promega) was 5' end labeled with 5 µCi [y-$^{32}$P]ATP (>5000 Ci/mmol, New England Nuclear Corp, Boston, Mass.) by incubaton with T4 polynucleotide kinase for 1 hr at 37° C. Unincorporated nucleotides were removed by passing the reaction mixture over 1 ml Sephadex G-5-spin column. Binding assays were performed at room temperature for 1 hr and consisted of 10 µg nuclear extract protein, 1 µg salmon sperm DNA, and 5×10$^4$ cpm of $^{32}$P labeled consensus of oligonucleotide in the presence and absence of fifty fold unlabeled oligonucleotide. DNA-protein complexes were resolved by 8% non denaturing polyacrylamide gel electrophoresis, the gels were dried onto filter paper and visualized by autoradiography.

TABLE 11

ENZYME ACTIVITY OF SELECTED REPRESENTATIVES OF THIS INVENTION

| R$_1$-X | R2 | R3 | IC50(µM) enzyme |
|---|---|---|---|
| 4-phenylbenzylamino | Isopropyl | Diethanolamino | 1.1 |
| 4-phenylbenzylamino | Isopropyl | Diethylamino | >2.4 |
| 4-phenylbenzylamino | Isopropyl | Ethanolamino | 2.5 |
| 4-bromoanilino | Isopropyl | Diethanolamino | 14 |
| 4-(3-methoxphenyl) benzylamino | Isopropyl | Diethanolamino | >10 |
| 4-(4-methoxphenyl) benzylamino | Isopropyl | Diethanolamino | 11 |
| 3-(4-nitrilophenyl) anilino | Isopropyl | Diethanolamino | 2.2 |
| 4-thiomethoxyanilino | Isopropyl | Diethanolamino | 12.4 |
| 4-(2-pyridinyl) benzylamino | Isopropyl | Diethanolamino | 4.5 |

The invention claimed is:

1. A compound having the formula:

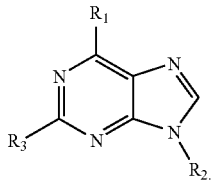

wherein $R_1$ is 3-quinolylamino, $R_2$ is isopropyl, and $R_3$ is diethanolamino, namely {(2-hydroxyethyl)[9-(methylethyl)-6-(3-quinolylamino)purin-2-yl]amino}ethan-1-ol.

2. A compound having the formula:

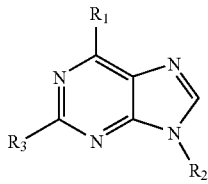

wherein $R_1$ is 4-chlorophenylmethylamino, $R_2$ is isopropyl, and $R_3$ is diethanolamino, namely 2-[(6-{[(4-chlorophenyl)methyl]amino}-9-(methylethyl)purin-2-yl)(2-hydroxyethyl)amino]ethan-1-ol.

3. A compound having the formula:

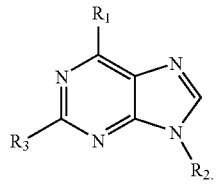

wherein $R_1$ is 2,5-difluorophenylmethylamino, $R_2$ is isopropyl, and $R_3$ is diethanolamino, namely 2-[(6-{[(2,5-difluorophenyl) methyl]amino}-9-(methylethyl)purin-2-yl)(2-hydroxyethyl)amino]ethan-1-ol.

* * * * *